US010695023B2

(12) United States Patent
Antoniades et al.

(10) Patent No.: US 10,695,023 B2
(45) Date of Patent: Jun. 30, 2020

(54) METHOD FOR CHARACTERISATION OF PERIVASCULAR TISSUE

(71) Applicant: OXFORD UNIVERSITY INNOVATION LIMITED, Botley, Oxford (GB)

(72) Inventors: Charalambos Antoniades, Headington (GB); Alexios Antonopoulos, Headington (GB); Stefan Neubauer, Headington (GB); Keith Channon, Headington (GB)

(73) Assignee: OXFORD UNIVERSITY INNOVATION LIMITED, Botley, Oxford (GB)

( * ) Notice: Subject to any disclaimer, the term of this patent is extended or adjusted under 35 U.S.C. 154(b) by 598 days.

(21) Appl. No.: 15/503,662

(22) PCT Filed: Aug. 14, 2015

(86) PCT No.: PCT/GB2015/052359
§ 371 (c)(1),
(2) Date: Feb. 13, 2017

(87) PCT Pub. No.: WO2016/024128
PCT Pub. Date: Feb. 18, 2016

(65) Prior Publication Data
US 2017/0265832 A1 Sep. 21, 2017

(30) Foreign Application Priority Data
Aug. 15, 2014 (GB) .................................. 1414496.8

(51) Int. Cl.
*A61B 6/00* (2006.01)
*A61B 6/03* (2006.01)

(52) U.S. Cl.
CPC ............ *A61B 6/5217* (2013.01); *A61B 6/032* (2013.01); *A61B 6/504* (2013.01)

(58) Field of Classification Search
CPC ........ A61B 6/032; A61B 6/504; A61B 6/5217
See application file for complete search history.

(56) References Cited

U.S. PATENT DOCUMENTS

2007/0242863 A1\* 10/2007 Hoppel ............... G06K 9/6222
382/128
2012/0076377 A1 3/2012 Dutta et al.
2012/0243764 A1 9/2012 Dey et al.

FOREIGN PATENT DOCUMENTS

CN 1403057 A 3/2003
CN 1726871 A 2/2006
(Continued)

OTHER PUBLICATIONS

Ross: Atherosclerosis an inflammatory disease, The New England Journal of Medicine, 340(2): 115-26 (1999).
(Continued)

*Primary Examiner* — Michael T Rozanski
(74) *Attorney, Agent, or Firm* — Merchant & Gould P.C.

(57) ABSTRACT

Methods for volumetric characterisation of perivascular adipose tissue use data collected by computed tomography (CT) scanning. The volumetric characterisation of perivascular adipose tissue allows the inflammatory status of underlying blood vessels to be established by CT scanning. This is of use in the diagnosis, prognosis and treatment of coronary and vascular disease.

38 Claims, 22 Drawing Sheets

(56) References Cited

FOREIGN PATENT DOCUMENTS

| CN | 101352349 A | 1/2009 |
|---|---|---|
| DE | 102013200163 A1 | 7/2014 |
| WO | 2006/085250 A2 | 8/2006 |

OTHER PUBLICATIONS

Major A.S. et al.: What fans the fire: insights into mechanisms of inflammation in atherosclerosis and diabetes, Circulation. 124(25): 2809-2811(2011).

Weintraub W.S. et al.: C-reactive protein, inflammation and atherosclerosis: do we really understand it yet?, European Heart Journal 21(12): 958-960 (2000).

Lee R et al.: Evaluating oxidative stress in human cardiovascular disease: methodological aspects and considerations, Current Medicinal Chemistry 19(16): 2504-20 (2012).

Margaritis M. et al.: Interactions Between Vascular Walls and Perivascular Adipose Tissue Reveal Novel Roles for Adiponectin in the Regulation of Endothelial Nitric Oxide Synthase Function in Human Vessels, Circulation. 127(22): 2209-2221 (2013).

Fifer K.M. et al., Positron Emission Tomography Measurement of Periodontal 18F-Fluorodeoxyglucose Uptake is Associated With Histologically Determined Carotid Plaque Inflammation, Journal of the American College of Cardiology 57(8): 971-976 (2011).

Greenland et al.: Coronary artery calcium score combined with Framingham score for risk prediction in asymptomatic individuals, Jama 291(2):210-215 (2004).

Alexopoulous N et al.: Effect of Intensive Versus Moderate Lipid-Lowering Therapy on Epicardial Adipose Tissue in Hyperlipidemic Post-Menopausal Women: A Substudy of the BELLES Trial, Journal of the American College of Cardiology 61(19):1956-1961 (2013).

Hoefer I.E. et al.: Novel methodologies for biomarker discovery in atherosclerosis, European Heart Journal 36 (39): 2635-2642 (2015).

Antoniades C. et al.: Adiponectin: from obesity to cardiovascular disease, Obesity reviews: an official journal of the International Association for the Study of Obesity 10(3): 269-279 (2009).

Antonopoulos A.S. et al.: 2015, Adiponectin as a Link Between Type 2 Diabetes and Vascular NADPH Oxidase Activity in the Human Arterial Wall: The Regulatory Role of Perivascular Adipose Tissue, Diabetes, 64(6): 2207-2219 (2015).

Ntambi J.M. et al: Adipocyte Differentiation and Gene Expression, The Journal of Nutrition 130(12): 3122S-3126S (2000).

Bassols J et al: Study of the Proinflammatory Role of Human Differentiated Omental Adipocytes, Journal of Cellular Biochemistry 107(6): 1107-1117 (2009).

Takaoka M et al.: Endovascular injury induces rapid phenotypic changes in perivascular adipose tissue, Atheroscler Thromb Vasc Biol 30: 1576-1582 (2010).

International Search Report for PCT/GB2015/052359, dated Oct. 22, 2015.

Office Action for Chinese Patent Application No. 201580048868.1, dated Oct. 12, 2019.

* cited by examiner

Left circumflex coronary artery

Femoral artery

METHOD FOR CHARACTERISATION OF PERIVASCULAR TISSUE

This application is a National Stage Application of PCT/GB2015/052359, filed 14 Aug. 2015, which claims benefit of British Patent Application No. 1414496.8, filed 15 Aug. 2014 and which applications are incorporated herein by reference. To the extent appropriate, a claim of priority is made to each of the above disclosed applications.

FIELD OF THE INVENTION

The present invention relates to perivascular tissue and methods for its characterisation.

BACKGROUND OF THE INVENTION

Perivascular adipose tissue (PVAT) surrounds (coronary) arteries and may be involved in local stimulation of atherosclerotic plaque formation. PVAT can be quantified using a number of techniques, including for example, echocardiography, computed tomography (CT) and magnetic resonance imaging (MRI). The quantity of PVAT correlates with some parameters of metabolic syndrome including increased waist circumference, hypertriglyceridemia and hyperglycemia, and with coronary atherosclerosis. PVAT has long been known to secrete pro-inflammatory proteins and induce inflammation of the artery wall. The long-held understanding of the pathology of atherogenesis in the vascular wall was that it is stimulated externally, and it was suggested that PVAT played a key role in this process.

Atherosclerosis is a progressive process in which an artery wall thickens as a result of invasion and accumulation of white blood cells. This inflammatory process results in plaques within the vessel wall containing living white blood cells, dead cell debris and fatty deposits including cholesterol and triglycerides.

Stable atherosclerotic plaques, which tend to be asymptomatic, are typically rich in extracellular matrix and smooth muscle cells, while unstable plaques are rich in macrophages and foam cells and the extracellular matrix separating the lesion from the arterial lumen (also known as the fibrous cap) is usually weak and prone to rupture. Ruptures of the fibrous cap eventually induce clot formation in the lumen, and such clots can block arteries or detach, move into the circulation and eventually block smaller downstream vessels causing thromboembolism. Chronically expanding plaques are frequently asymptomatic until vessel occlusion (stenosis) is severe enough that blood supply to downstream tissue is insufficient.

Atherosclerosis is asymptomatic for decades because the arteries enlarge at all plaque locations and blood flow is not immediately affected. Indeed, plaque ruptures are also asymptomatic unless they result in sufficient narrowing or closure of an artery that impedes blood flow to different organs so as to induce symptoms. Typically, the disease is only diagnosed when the patient experiences other cardiovascular disorders such as stroke or heart attack. Symptomatic atherosclerosis is typically associated with men in their 40s and women in their 50s to 60s. Sub-clinically, the disease begins to appear in childhood, and noticeable signs can begin developing at puberty. While coronary artery disease is more prevalent in men than women, atherosclerosis of the cerebral arteries and strokes equally affect both sexes.

Atherosclerosis may cause narrowing in the coronary arteries, which are responsible for bringing oxygenated blood to the heart, and this can produce symptoms such as the chest pain of angina, shortness of breath, sweating, nausea, dizziness or light-headedness, breathlessness or palpitations. Cardiac arrhythmias may also result from cardiac ischemia. Atherosclerosis that causes narrowing in the carotid arteries, which supply blood to the brain and neck, can produce symptoms such as a feeling of weakness, not being able to think straight, difficulty speaking, becoming dizzy and difficulty in walking or standing up straight, blurred vision, numbness of the face, arms, and legs, severe headache and losing consciousness. These symptoms may also be present in stroke, which is caused by marked narrowing or closure of arteries going to the brain leading to brain ischemia and death of cells in the brain. Peripheral arteries, which supply blood to the legs, arms, and pelvis may also be affected. Symptoms can include numbness within the affected limbs, as well as pain. Plaque formation may also occur in the renal arteries, which supply blood to the kidneys. Plaque occurrence and accumulation leads to decreased kidney blood flow and chronic kidney disease, which, like all other areas, are typically asymptomatic until late stages.

Inflammation is pivotal in atherogenesis (Ross R (1999). Atherosclerosis—an inflammatory disease. *N Engl J Med* 340(2):115-26; and Major A S, and Harrison D G (2011). What fans the fire: insights into mechanisms of inflammation in atherosclerosis and diabetes mellitus. *Circulation* 124(25):2809-11) and modalities that can accurately detect vascular inflammation at an early stage would enable better cardiovascular risk stratification and implementation of appropriate therapeutic interventions. Current tools to assess vascular inflammation that rely on systemic plasma biomarkers (e.g. C-reactive protein, pro-inflammatory cytokines) are not directly related to the process of atherogenesis (Weintraub W S, and Harrison D G (2000). C-reactive protein, inflammation and atherosclerosis: do we really understand it yet? *Eur Heart J* 21(12):958-60), and provide very poor associations with local vascular biological processes (Lee R, Margaritis M, Channon K M, and Antoniades C (2012). Evaluating oxidative stress in human cardiovascular disease: methodological aspects and considerations. *Current medicinal chemistry* 19(16):2504-20; and Margaritis M, Antonopoulos A S, Digby J, Lee R, Reilly S, Coutinho P, Shirodaria C, Sayeed R, Petrou M, De Silva R, et al (2013). Interactions between vascular wall and perivascular adipose tissue reveal novel roles for adiponectin in the regulation of endothelial nitric oxide synthase function in human vessels. *Circulation* 127(22):2209-21). Moreover, existing imaging tools (invasive such as intravascular ultrasound/optical coherence tomography or non-invasive such as Computerized Tomography (CT) Angiography/fluorodeoxyglucose(18F)-positron emission tomography) are unable to provide reliable information on vascular inflammation in human coronary arteries (Fifer K M, Qadir S, Subramanian S, Vijayakumar J, Figueroa A L, Truong Q A, Hoffmann U, Brady T J, and Tawakol A (2011). Positron emission tomography measurement of periodontal 18F-fluorodeoxyglucose uptake is associated with histologically determined carotid plaque inflammation. *Journal of the American College of Cardiology* 57(8):971-6). Coronary calcium scoring (CCS) is the only non-invasive imaging biomarker with predictive value in primary prevention (Greenland P, LaBree L, Azen S P, Doherty T M, and Detrano R C (2004). Coronary artery calcium score combined with Framingham score for risk prediction in asymptomatic individuals. *Jama* 291(2):210-5), but it describes non-reversible structural changes of the vascular wall, and it is not altered by interventions that reduce cardiovascular risk (e.g. statins) (Alexopoulos N, Melek B H, Arepalli C D, Hartlage G R, Chen Z, Kim S, Stillman A E, and Raggi P (2013). Effect of intensive versus moderate lipid-lowering therapy on epicardial adipose tissue in hyperlipidemic post-menopausal women: a substudy of the BELLES trial (Beyond Endorsed Lipid Lowering with EBT Scanning). *Journal of the American College of Cardiology* 61(19): 1956-61). A novel imaging biomarker that could overcome these limitations and non-invasively detect vascular inflammation would be invaluable in clinical research and risk stratification of coronary artery disease (Hoefer I F, Steffens S, Ala-Korpela M, Back M, Badimon L, Bochaton-Piallat M L, Boulanger C M, Caligiuri G, Dimmeler S, Egido J, et al (2015). Novel methodologies for biomarker discovery in atherosclerosis. *Eur Heart J* 2015 Jun. 5. pii: ehv236[Epub ahead of print]).

It has recently become clear that vascular inflammation and oxidative stress has the ability to affect the biology of PVAT as the vascular wall releases mediators able to exert a paracrine effect on the neighbouring PVAT (see e.g. Margaritis et al. Circulation 2013; 127(22):2209-21). This observation was in contrast to the classical theory according to which PVAT sends paracrine signals to the vascular wall. It is now understood that the biology of PVAT is shaped by signals received from the blood vessel it surrounds, and characterisation of that PVAT can provide useful information regarding the biology and health of that blood vessel.

Adipose tissue releases a wide range of bioactive molecules that exert endocrine and paracrine effects on the vascular wall (Antoniades C, Antonopoulos A S, Tousoulis D, and Stefanadis C (2009). Adiponectin: from obesity to cardiovascular disease. *Obesity reviews: an official journal of the International Association for the Study of Obesity* 10(3):269-79), but we have recently suggested that the communication between adipose tissue and the vascular wall is bi-directional (Margaritis M, Antonopoulos A S, Digby J, Lee R, Reilly S, Coutinho P, Shirodaria C, Sayeed R, Petrou M, De Silva R, et al (2013). *Circulation* 127(22):2209-21; and Antonopoulos A S, Margaritis M, Coutinho P, Shirodaria C, Psarros C, Herdman L, Sanna F, De Silva R, Petrou M, Sayeed R, et al (2015). Adiponectin as a link between type 2 diabetes and vascular NADPH oxidase activity in the human arterial wall: the regulatory role of perivascular adipose tissue. *Diabetes* 64(6):2207-19). The biological properties of adipose tissue are largely driven by the degree of differentiation of small, immature pre-adipocytes to large, well-differentiated adipocytes, rich in intracellular lipid droplets (Ntambi J M, and Young-Cheul K (2000). Adipocyte differentiation and gene expression. *The Journal of nutrition* 130(12):3122S-6S). This differentiation of pre-adipocytes is orchestrated by PPAR-γ activation, a transcription factor supressed by exogenous inflammation (Bassols J, Ortega F J, Moreno-Navarrete J M, Peral B, Ricart W, and Fernandez-Real J M (2009). Study of the proinflammatory role of human differentiated omental adipocytes. *Journal of cellular biochemistry* 107(6):1107-17). There is no established non-invasive method to monitor adipocyte size in human adipose tissue.

Previous efforts to analyse the quantity of human adipose tissue depots by computed tomography have produced only limited data on the assessment of PVAT quality by imaging. One such attempt to assess the "quality" of pericoronary adipose tissue has been reported (Konishi et al. Atherosclerosis 2011). In that study "adipose tissue density" was quantified in arbitrarily selected 10 mm$^2$ areas in 2D CT images, and a pericoronary CT gradient (PDG) was defined using radiodensity values determined for PVAT, arbitrarily defined as falling within 5 mm of the wall of the coronary artery, non-perivascular adipose tissue (non-PVAT), arbitrarily defined as falling more than 10 mm from the wall of the coronary artery. This approach remains a quantitative one that is prone to subjective bias, relying as it does on the judgment of the individual analysing the CT image data to select appropriate regions for analysis.

Despite the high incidence and asymptomatic nature of much vascular disease, there remains an urgent need for a tool that permits objective, non-invasive characterisation of PVAT. Available techniques provide information about the quantity of PVAT surrounding a blood vessel, but this data does not characterise the measured PVAT and it cannot discriminate between pathologies. Therefore, there is a requirement for a specific and sensitive tool to accurately characterize PVAT around a blood vessel.

SUMMARY OF THE INVENTION

The present invention is based on the surprising finding by the inventors that vascular inflammation and oxidative stress has the ability to affect the biology of PVAT as the vascular wall releases mediators able to exert a paracrine effect on the neighbouring PVAT. The present invention provides methods for the volumetric characterisation of perivascular tissue using data gathered from a computerised tomography scan, and it also provides the use of such methods in the identification and diagnosis of vascular disease. The methods provided by the invention are not dependent on the volume of PVAT and are therefore less prone to confounders related to adipose tissue expansion, and by taking account of vessel diameter they allow detection of early changes in PVAT that may precede the development of vascular disease.

According to a first aspect, the invention provides a method for volumetric characterisation of perivascular tissue using data gathered from a computed tomography (CT) scan along a length of a blood vessel, the method comprising: quantifying radiodensity in each of one or more concentric layers of perivascular tissue; and determining whether one or more of the quantified radiodensity values are above or below a baseline radiodensity value.

According to a second aspect, the invention provides a method for volumetric characterisation of perivascular tissue using data gathered from a CT scan along a length of a blood vessel, the method comprising: determining a plot of the fold change in quantified radiodensity relative to baseline radiodensity in each of one or more concentric layers of perivascular tissue with respect to distance from the outer wall of the blood vessel up to an end distance; determining the area of the region bound by the plot of fold change in quantified radiodensity and a plot of baseline radiodensity with respect to distance from the outer wall of the blood vessel up to the end distance; and dividing said area by the quantified radiodensity measured at a distance from the outer wall of the blood vessel, wherein the distance is less than the radius of the vessel or is a distance from the outer surface of the vessel above which the quantified radiodensity of adipose tissue drops by more than 5% compared to the baseline radiodensity of adipose tissue in a vessel of the same type free of disease, where the baseline radiodensity of adipose tissue is a value determined from the first 1 mm-thick layer surrounding the outer vessel wall.

According to further aspects, the invention provides the use of a method for volumetric characterisation of perivascular tissue using data gathered from a CT scan along a length of a blood vessel, the method comprising: quantifying radiodensity in each of one or more concentric layers of perivascular tissue; and determining whether one or more of the quantified radiodensity values are above or below a baseline radiodensity value, in the diagnosis of vascular disease.

DESCRIPTION OF THE DRAWINGS

The invention is described with reference to the following Tables and Figures in which:

FIGS. 13A-D demonstrate that EpAT and ThAT contain significantly smaller adipocytes compared to ScAT (n=7 patients). FIGS. 13E-G show gene expression studies in tissue from the entire cohort in study arm 1 (n=453), higher gene expression of peroxisome proliferation activated receptor-γ (PPAR-γ, a marker of the early phase of adipocyte differentiation, FIG. 13E), CEBPA (marker of the late phase of adipocyte differentiation, FIG. 13F) and FABP4 (marker of terminal adipocyte differentiation, FIG. 13G) is measured in ScAT compared to EpAT or ThAT.

FIG. 15A shows a strong correlation between QR in contrast vs non-contrast CT images. FIG. 15B shows there was no significant difference in absolute values of QR between contrast and non-contrast CT images.

FIG. 16A-D shows that pro-inflammatory cytokines inhibit pre-adipocyte differentiation to mature adipocytes as determined by their morphological changes and their lack of accumulation of lipid droplets demonstrated by oil-red-O staining. FIG. 16E shows photometric quantification of the oil-red-O staining measurements. FIG. 16F-I show that cytokines triggered pre-adipocytes proliferation (F) and suppressed gene expression of the differentiation markers peroxisome proliferator-activated receptor-γ (PPAR-γ; G), CCAAT/enhancer binding protein alpha (CEBPA; H) and Fatty acid binding protein-4 (FABP4; I) in these cells. *p<0.05, **p<0.01 vs control group.

FIGS. 17A-F show strong inverse correlation between QR values and expression levels of CEBPA (a marker of the late phase of adipocyte differentiation) and FABP4 (a marker of terminal adipocyte differentiation) in the same explants in all adipose tissue depots. FIG. 17G shows inverse correlation between adipocyte size and the measured in vivo QR value in adipose tissue explants. FIGS. 17H-I show in vivo QR of adipose tissue strongly associated with the QR of the adipose tissue explants, collected from the same patients during surgery, in both EpAT and ScAT.

FIGS. 18A-D show strong inverse correlation between QR values and expression levels of CEBPA (a marker of the late phase of adipocyte differentiation) and FABP4 (a marker of terminal adipocyte differentiation) in the same explants in all adipose tissue depots.

FIGS. 20A-C show that peri-coronary adipose tissue close to the RCA expressed significantly lower levels of PPAR-γ, CEBPA and FABP4 (markers of early, late phase and terminal adipocyte differentiation respectively). FIG. 20D shows histological data demonstrating that adipocytes of the peri-coronary adipose tissue close to the RCA were significantly smaller than those further from the RCA. FIGS. 20E-H show determination of average adipose tissue radiodensity (Quantified Radiodensity, QR) values around the RCA of patients undergoing clinical CT angiography in Study Arm 3 (n=273). QR was calculated as the average radiodensity of the fat (−190 to −30 Hounsfield Units) for each cylindrical 1 mm-thick layer of peri-coronary tissue around the RCA, for a radial distance from RCA wall 1 mm to 20 mm. FIG. 20I shows that there was a drop in measured QR values as the scan moved from close to the vessel to tissue away from it, reflecting the changes in adipocyte differentiation status and size. A significant difference is evident when the QR value is plotted against the distance from RCA outer wall for patients with coronary artery disease (n=156) and patients with healthy coronaries (n=117). *$p<0.05$ vs 1 mm FIGS. 21A-B show that patients with high $QR_{PVAT}$ and VPCI % values around the RCA had higher total calcium scores, but was no correlation between either $QRP_{VAT}$ or VPCI % with calcification volume in the underlying RCA. Calcium volume was defined as the vascular wall volume occupied by voxels with attenuation >465 HU. FIGS. 21C-D show that higher $QR_{PVAT}$ and VPCI % values around the RCA were associated with higher atherosclerotic plaque burden in patients without CAD (defined as atherosclerotic plaque burden in the top tertile) and were further increased in CAD patients. FIGS. 21E-F show that in CAD patients with presence of atherosclerotic plaques in the underlying RCA segment (atherosclerotic plaque burden in proximal RCA within the top 2 tertiles), VPCI % (but not $QRI_{PVAT}$) was significantly higher in the presence of soft plaques (calcification volume=0) compared to mixed or calcified plaques.

DETAILED DESCRIPTION OF THE INVENTION

Figure 1:
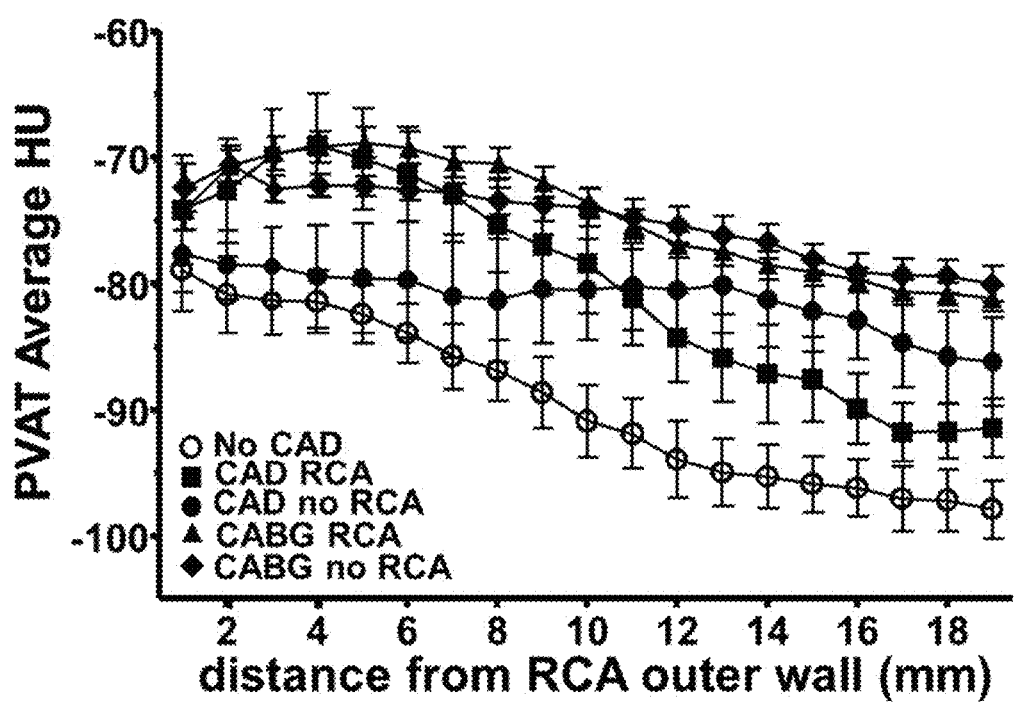
FIG. 1 shows volumetric characterization of the right coronary artery. The vascular wall was scanned over a 40 mm-distance, in the proximal part of the right coronary artery (RCA, 1 cm distal to the right ostium) in coronary CT angiographs from 70 subjects: subjects without coronary artery disease (no CAD, n=10), CAD patients with right coronary disease (RCA) disease (CAD RCA, n=10), CAD patients without RCA disease (CAD no RCA, n=8), patients post-coronary artery bypass grafting (CABG) with RCA disease (CABG RCA, n=29) and post-CABG patients with no RCA disease (CABG no RCA, n=13). Perivascular tissue was segmented into 1 mm-thick serial concentric layers extending to a 20 mm distance from the outer wall of the artery. Radiodensity values were calculated for each individual layer and plotted against the distance from the outer wall of the RCA for each group. Radiodensity decreased with increasing distance away from RCA wall in all groups, but the pattern of radiodensity drop was significantly different between groups. P-values were calculated from repeated measures ANOVA.

The present inventors have discovered that the 'pattern' of change in the radiodensity of PVAT over a specified distance from the outer vascular wall provides valuable information about the blood vessel. The present invention provides both a method for volumetric characterisation of perivascular tissue and methods of diagnosing vascular disease that are not dependent of the volume of PVAT and therefore less prone to confounders related to adipose tissue expansion. The methods provided are advantageous as they provide clinicians with an objective assessment of a patient's vascular health without the need for any invasive testing procedures. Using the methods of the invention, each patient's vascular health can be quantitatively assessed so as to permit diagnosis and identification of any need for further testing. As a result, vascular disease can be identified in asymptomatic patients and treated earlier and more effectively, treatment can be followed up more effectively, further investigational and therapeutic intervention can be directed more appropriately, and resources in the healthcare system can be better managed. Furthermore, the invention enables stratification of patients' vascular health, allowing targeted therapeutic intervention, leading to improved patient outcomes at reduced costs.

The method for volumetric characterisation of perivascular tissue involves the use of data gathered from a computed tomography scan along a length of a blood vessel, and comprises two steps: quantifying radiodensity for each of one or more concentric layers of perivascular tissue; and determining whether one or more of these radiodensity values are above or below a baseline radiodensity value.

Perivascular tissue is detected in a computed tomography (CT) scan of a specified length of a blood vessel using image analysis software. The perivascular tissue is then subjected to a volumetric segmentation into a number of concentric layers that are coaxial with the blood vessel, and the radiodensity of PVAT within each concentric layer is calculated. Voxels containing PVAT are identified by applying specific radiodensity thresholds, from −190 to −30 HU, that exclude non-adipose tissue from the analysis, and a radiodensity of PVAT-containing voxels within each concentric layer is determined. The radiodensity value determined for each of one or more individual concentric layers is then compared to a baseline PVAT radiodensity value determined from the same CT scan dataset. In this way a comprehensive, fully volumetric characterization of the adipose tissue lying around a blood vessel can be performed without relying on arbitrary spatial definitions of 'perivascular' and using objective measurement of radiodensity using Hounsfield Units. Comparison of the determined radiodensity of PVAT to a baseline PVAT radiodensity for more than one concentric layer provides a clear indication of the status of PVAT deposits with respect to distance from the blood vessel wall.

The term "perivascular tissue" in the context of the present invention is understood to the tissue that surrounds a blood vessel. Perivascular tissue may include perivascular adipose tissue.

In the context of the present invention, a "computed tomography scan" is understood to be a scan generated using computer-processed x-rays to produce tomographic images of specific areas of the scanned perivascular region. The term "computed tomography scan" is synonymous with the terms CT scan and CAT scan.

Radiodensity, measured in Hounsfield units (HU), is a measure of the relative inability of X-rays to pass through material. Measurement of radiodensity values allows tissue types to be distinguished in CT on the basis of their different radio-opacities. Fat is not very radiodense, and it typically measures between −190 and −30 HU while muscle, blood and bone measure between +10 and +40, between +30 and +45, and between +700 and +3000 HU respectively.

In the context of the present invention, the term "baseline radiodensity" is understood to be a radiodensity value determined from the first 1 mm-thick layer surrounding the outer vessel wall. This value can be determined from a representative voxel or population of voxels within the 1 mm thick layer, for example, those voxels containing adipose tissue or water. The baseline can be determined from any of the one or more concentric layers of perivascular tissue that are analysed. Preferably, the baseline radiodensity value is an "average" radiodensity value calculated from a population of voxels in that layer. It is understood that a baseline radiodensity value can be calculated using the same CT data used to determine the radiodensity in the each of one or more concentric layers of perivascular tissue, but it is also understood that a baseline radiodensity value may be calculated based on data collected from a population of CT scan datasets.

In the context of the present invention, an "average" value is understood to mean a central or typical value, and it can be calculated from a sample of measured values using formulas that are widely known and appreciated in the art. Preferably, the average is calculated as the arithmetic mean of the sample of radiodensity values, but it can also be calculated as the geometric mean, the harmonic mean, the median or the mode of a set of collected radiodensity values. The average value may be calculated by reference to data collected from all voxels within a concentric tissue layer or by reference to a selected population of voxels within the concentric tissue layer, for example water- or adipose tissue-containing voxels.

In the context of the present invention, the term "concentric layers of perivascular tissue" is understood to mean coaxial layers of perivascular tissue surrounding a blood vessel, each concentric layer being concentric and lying at a constant distance from the outer wall of a blood vessel.

Preferably the CT scan of a section of a blood vessel is carried out using routine methods and commercially available instruments.

In a first aspect, the present invention provides a method for volumetric characterisation of perivascular tissue using data gathered from a computed tomography scan along a length of a blood vessel, comprising quantifying radiodensity in each of one or more concentric layers of perivascular tissue and determining whether one or more of the quantified radiodensity values are above or below a baseline radiodensity value. The radiodensity of each voxel within each of one or more concentric layers of perivascular tissue can be determined, and by selecting specific radiodensity ranges it is possible to provide a volumetric characterisation of distinct materials and tissue types within those layers. Selection of those voxels with radiodensity values between −190 and −30 Hounsfield units (HU) restricts the quantification to those voxels representing adipose tissue within the layer. Selection of those voxels with radiodensity values between −15HU and +15HU restricts the quantification to those voxels representing water within the layer. By applying these specific thresholds all voxels corresponding to adipose tissue or water can be analysed and adipose tissue surrounding a vascular segment can be characterised. The radiodensity of the selected volumetric dataset that correspond to adipose tissue provides information on the composition of adipose tissue with higher radiodensity indicating the presence of smaller adipocytes, while more water suggests increased levels of inflammation within the tissue.

In one particular embodiment, the present invention provides the method using data gathered from a computed tomography scan along a length of a blood vessel, for volumetric characterisation of perivascular adipose tissue by selecting those voxels having radiodensity values between −190HU and −30HU for quantification of a radiodensity value that is compared to the baseline value.

In another particular embodiment, the present invention provides the method using data gathered from a computed tomography scan along a length of a blood vessel, for volumetric characterisation of water content in perivascular tissue by selecting those voxels having radiodensity values between −15HU and +15HU for quantification of a radiodensity value that is compared to the baseline value.

The quantified radiodensity value can be provided as an average value to permit comparison of values from tissue layers having different volumes. Average values are typically calculated as simple arithmetic means of the sample of radiodensity values measured from individual voxels within each layer.

The method of the present invention may be used to provide a volumetric characterisation of perivascular tissue surrounding any blood vessel using the data gathered from a CT scan. In particular embodiments the method is used to characterise the perivascular tissue surrounding the right coronary artery and the perivascular tissue surrounding the aorta. Layers of any suitable thickness may be chosen for analysis according the method of the present invention. However, it is very desirable to provide a high resolution characterisation of the perivascular tissue, and this is achieved by subjecting thinner concentric layers of tissue to the methods of the present invention. In one particular embodiment the layers are 1 mm thick.

One convenient way of summarising the volumetric characterisation of perivascular tissue using the method of the present invention is by representing it as one or more single values. Accordingly, the inventors have defined the Volumetric Perivascular Tissue Characterization Index-integral (VPCI-$i_a$) and VPCI (%) to define the pattern of change in perivascular tissue over a specified radial distance (a) from the blood vessel wall. The fold changes in the quantified radiodensity relative to baseline radiodensity in each of one or more concentric layers of perivascular tissue are plotted against the distance of each of the one or more concentric layers from the vessel wall. The quantified radiodensity measured in any appropriate layer may serve as the baseline. It is most convenient to select the quantified radiodensity value measured in the tissue layer lying in direct contact with the blood vessel as the baseline radiodensity value. The area of the region bound by the plot of fold change in quantified radiodensity and a plot of baseline radiodensity with respect to distance from the outer wall of the blood vessel is calculated, and this value is divided by a quantified radiodensity value measured at a specified distance (y) from the blood vessel wall. The calculation of VPCI-$i_a$/VPCI (%) can be represented mathematically as follows:

$$VPCI\text{-}i_a = \frac{\int_1^a h(B) - h(x) dx}{|h(y)|}$$

$$VPCI(\%)_a = \frac{100 * [(h(B) - h(x)]}{h(x)}$$

Where

VPCI-$i_a$ is Volumetric Perivascular Tissue Characterization Index integral up to radial distance 'a' mm from outer vessel wall VPCI (%)$_a$ Is the percent change in quantified radiodensity to a radial distance 'a' mm from outer vessel wall x is radial distance from outer vessel wall (in mm)

h(x) is quantified radiodensity at 'x' mm radial distance h(B) is the baseline radiodensity B is the distance in mm from outer wall of the blood vessel defining the 'Baseline'

Figure 2:
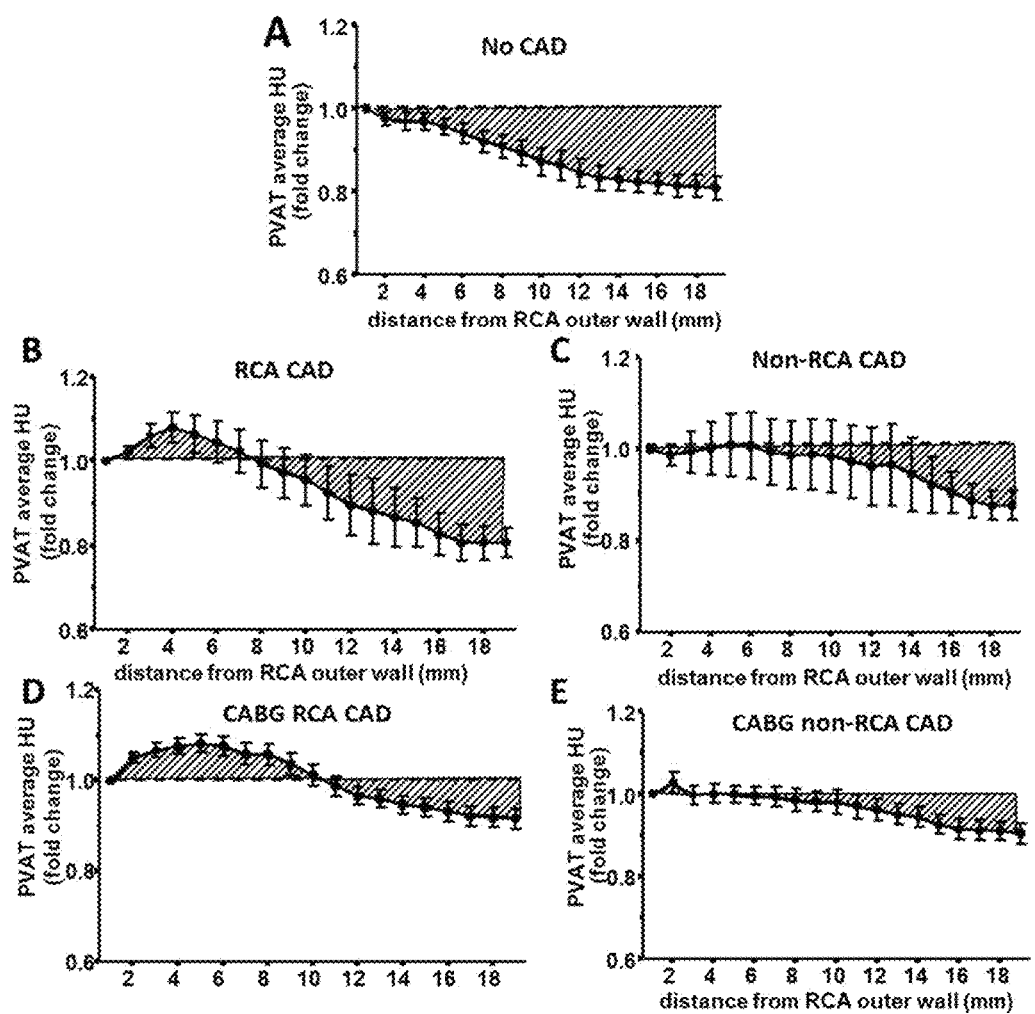
FIG. 2 shows the pattern of radiodensity change of perivascular adipose tissue around the right coronary artery for various disease states. Radiodensity values of adipose tissue were calculated for each concentric 1-mm thick layer around the outer wall of the right coronary artery and plotted as fold changes with respect to distance from the outer wall of the vessel. A) No CAD=subjects without coronary artery disease (n=10), B) RCA-CAD=patients with RCA disease (n=10), C) non-RCA CAD=patients with CAD but without RCA disease (n=8), D) CABG RCA CAD=CAD patients post-coronary artery bypass grafting (CABG) with RCA disease (n=29), and E) CABG non-RCA CAD=CAD patients post-CABG with no RCA disease (n=13).
Figure 3:
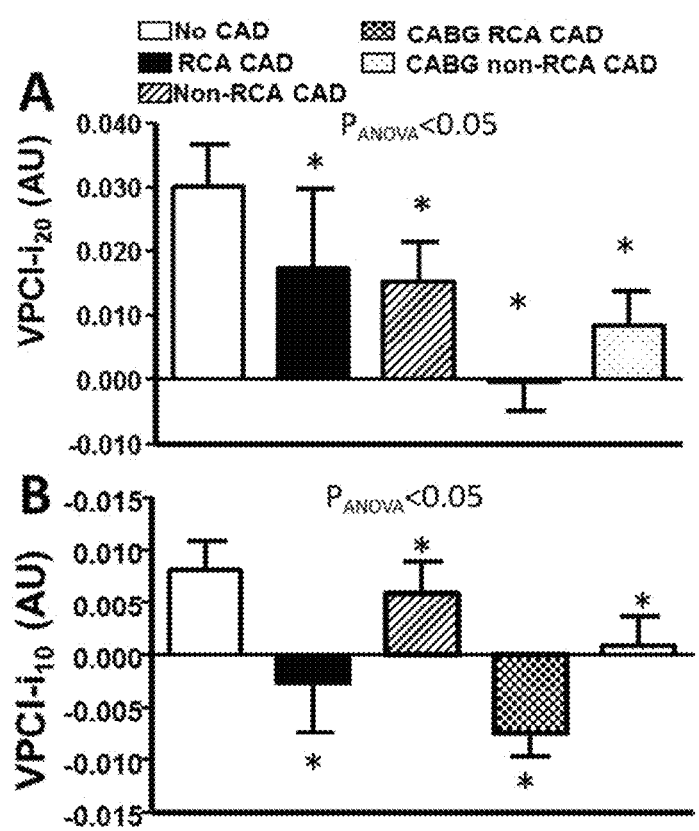
FIG. 3 shows that Volumetric Perivascular Characterisation Index (VPCI-i) predicts presence of coronary artery disease. The plots of radiodensity change of perivascular adipose tissue around the right coronary artery with respect to distance from the outer wall of the vessel (FIG. 2) were used to calculate the area under the curve (AUC) by using the horizontal line passing through y=1 as the baseline (radiodensity expressed as fold changes). The AUC below baseline was given positive values, while the AUC above baseline was given negative values, plotted as shaded areas for each group of patients (A to E). The algebraic sum of AUCs divided by the absolute value of the radiodensity of PVAT (adipose tissue lying in a distance equal to the radius of the vessel around the outer vascular wall) was used to calculate VPCI-i for each group. VPCI-i$_{20}$ (A) and VPCI-i$_{10}$ (B) were significantly different between patient groups. Statistical comparisons of VPCI-i$_{20}$ and VPCI-i$_{10}$ between groups were performed with MedCalc®, by using 2-way ANOVA for [distance]×[group] interaction after Bonferroni correction for comparisons between 5 groups. *p<0.05 vs no CAD group.

|h(y)| is absolute value of the quantified radiodensity measured at a specified distance, y, from the blood vessel wall The radial distance (a) for which the pattern of change in perivascular tissue radiodensity is calculated can be the distance from the outer surface of a healthy vascular wall at which PVAT radiodensity reaches the minimum value for the scanned anatomical area or a >10% drop below the baseline radiodensity value, where baseline radiodensity is a radiodensity value of adipose tissue determined from the first 1 mm-thick concentric layer surrounding the outer vessel wall. The present inventors have discovered that calculation of VPCI-$i_{10}$ and VPCI-$i_2$ values provide particularly useful information concerning the health of blood vessels. VPCI-$i_{10}$ and VPCI-$i_{20}$ values predict the presence of coronary artery disease (CAD) and are significantly lower in subjects with CAD compared to high risk subjects without CAD (see FIGS. 1 and 2). VPCI-$i_{10}$ is more sensitive to identify vessels with atherosclerosis while VPCI-$i_{20}$ is superior in identifying coronary atherosclerosis in general, even if there is no significant disease in the underlying vessel (See FIG. 3). The use of VPCI-i indices is useful for the characterization of the tissue around any vessel including the right coronary artery, the left coronary system, and other vascular beds including the aorta and the femoral artery.

It is useful to distinguish between perivascular adipose tissue (PVAT) and non-perivascular adipose tissue (non-PVAT). This distinguishes adipose tissue that lies close to the blood vessel from adipose tissue that lies further away from the blood vessel and cannot therefore be considered perivascular. A major problem facing the field until now was the lack of a meaningful definition of PVAT. By using a volumetric segmentation of perivascular tissue, the present invention provides such a definition of PVAT as the adipose tissue lying within a distance equal to the radius of the vessel from the outer wall or equal to the point where the radiodensity of adipose tissue drops by more than 5% compared to the baseline radiodensity of adipose tissue in a vessel of the same type free of disease, where the baseline radiodensity of adipose tissue is a value determined from the first 1 mm-thick layer surrounding the outer vessel wall. Distinction between the two adipose tissue types allows determination of another useful index of vascular health, the Volumetric Perivascular Characterisation Index (VPCI), which can be calculated by subtracting the quantified radiodensity in a layer of perivascular tissue from the quantified radiodensity in a layer of non-perivascular tissue. In a particular embodiment, the quantified radiodensity in a layer of perivascular tissue is measured at a distance equal to the radius of the vessel around the outer wall of the blood vessel. In a further particular embodiment, the quantified radiodensity in a layer of non-perivascular tissue is measured at a layer lying at a distance equal from two to three times the size of the average radius of the vessel around the outer wall of the blood vessel. The calculation of VPCI can be represented mathematically as follows:

$$VPCI = [QR_{PVAT} - QR_{nPVAT}].$$

Where

VPCI is Volumetric Perivascular Characterization Index $QR_{PVAT}$ is quantified radiodensity in a layer of perivascular tissue $QR_{nPVAT}$ is quantified radiodensity in a layer of non-perivascular tissue Or VPCI can be expressed as the % change in $QR_{PVAT}$ from $QR_{nPVAT}$ using the following formula:

$$VPCI (\%) = [100 * (QR_{PVAT} - QR_{nPVAT})] / QR_{PVAT}$$

The inventors have discovered that stratification of VPCI values on a scale having a lower threshold and an upper threshold allows assignment of a volumetric perivascular tissue characterisation score (VPCS) to each blood vessel. A VPCS of I is assigned where VPCI values are equal to or below the lower threshold, a VPCS of II is assigned where VPCI values are above the lower threshold but below the upper threshold, and a VPCS of III is assigned where VPCI values are equal to or above the upper threshold. In a particular embodiment, the present invention provides a VPCS scale where the lower threshold value is 2.0 and the upper threshold value is 8.0.

The VPCI-i indices for the characterisation of perivascular tissue (VPCI-$i_a$ and VPCS) can be applied to blood vessels to assess their health status.

Coronary vessels that have a higher VPCS, VPCI (%) and lower VPCI-$i_a$ score can be diagnosed as "diseased" and therefore differentiated from healthy coronary vessels that are free of disease. These indices are also useful in predicting the progression rate of coronary atherosclerosis. Moreover, characterisation of the pericoronary adipose tissue of subjects without known coronary artery disease can provide valuable prognostic information for the risk of developing coronary artery disease, even at an early stage, over and above coronary calcium score which is currently the sole established CT imaging biomarker that provides such prognostic information.

Figure 12:
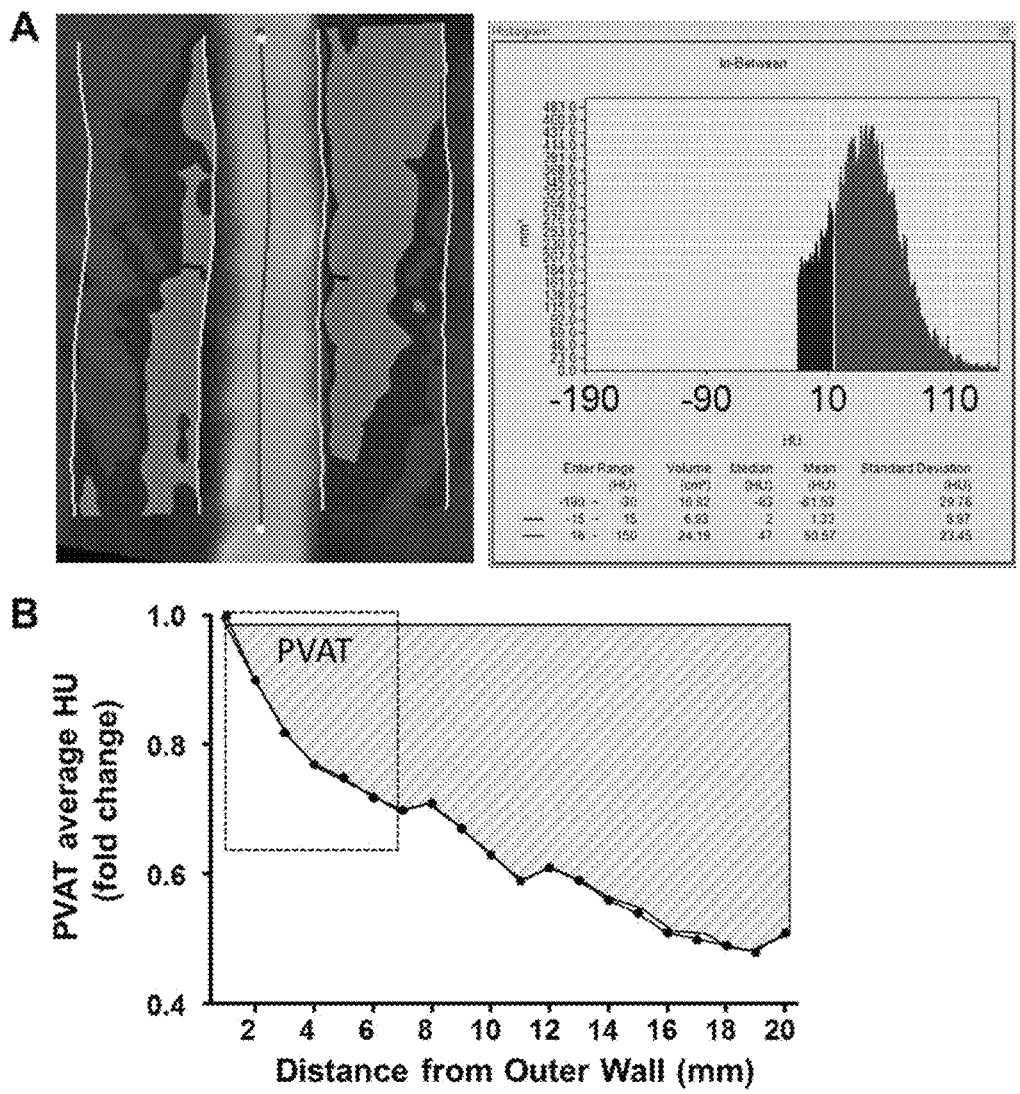
FIG. 12 shows volumetric characterization of perivascular tissue around the right femoral artery. Voxels corresponding to PVAT (−190HU to −30HU), corresponding to water (−15HU to +15HU) and corresponding to non-adipose tissue (+15 to +120HU) are shown (A). Perivascular tissue was segmented into 1 mm-thick serial concentric layers extending to a 20 mm distance from the outer wall of the artery. PVAT was defined as the adipose tissue lying within a distance equal to the radius of the vessel, and the quantified radiodensity of PVAT in each concentric layer is plotted as fold change compared to baseline radiodensity against the distance from the outer vessel (B).
Figure 13:
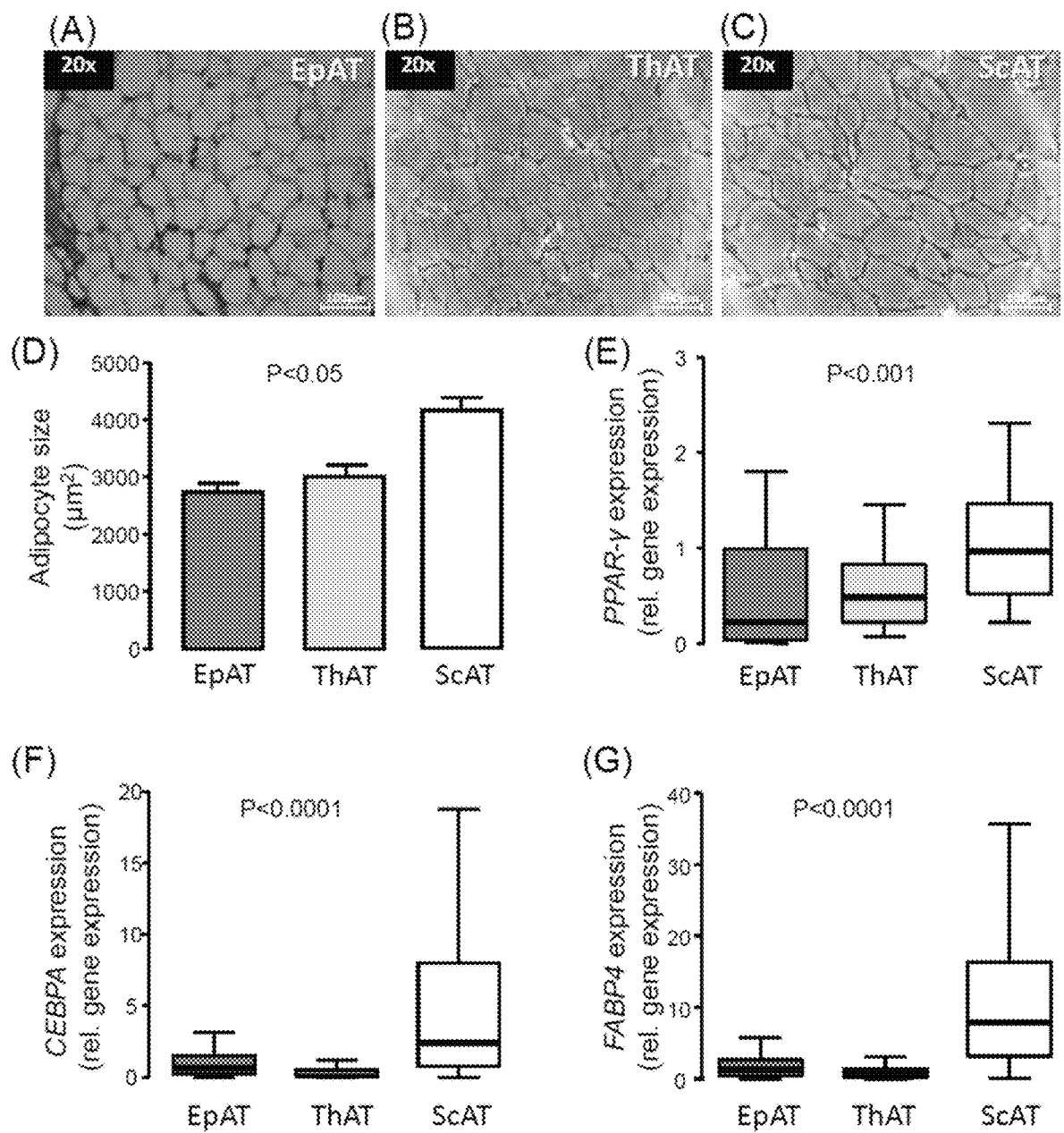
FIG. 13 shows histological analysis of Epicardial (EpAT), thoracic (ThAT) and subcutaneous (ScAT) adipose tissue biopsies in study arm 1.

Another useful application of the $QR_{PVAT}$, VPCI (%) and VPCI-i indices relates to subclinical atherosclerosis and its progression rate. Currently clinicians assess the intima-media thickness of the carotid arteries (arteries of the neck), as an index of subclinical atherosclerosis, as it is a strong predictor of future cardiovascular events. $QR_{PVAT}$, VPCS, VPCI (%) and VPCI-$i_a$ can be calculated for the perivascular tissue of carotid arteries and they can provide valuable information about the progression rate of subclinical atherosclerosis. This will help clinicians to collect additional prognostic information about the risk of atherosclerosis development at a very early stage before the onset of any clinical symptoms. Similarly, the perivascular tissue of peripheral arteries (See e.g. femoral artery, FIG. 12) can be assessed to collect prognostic information about the risk of developing peripheral arterial disease or its progression rate in subjects without or with established peripheral arterial disease respectively.

Figure 10:
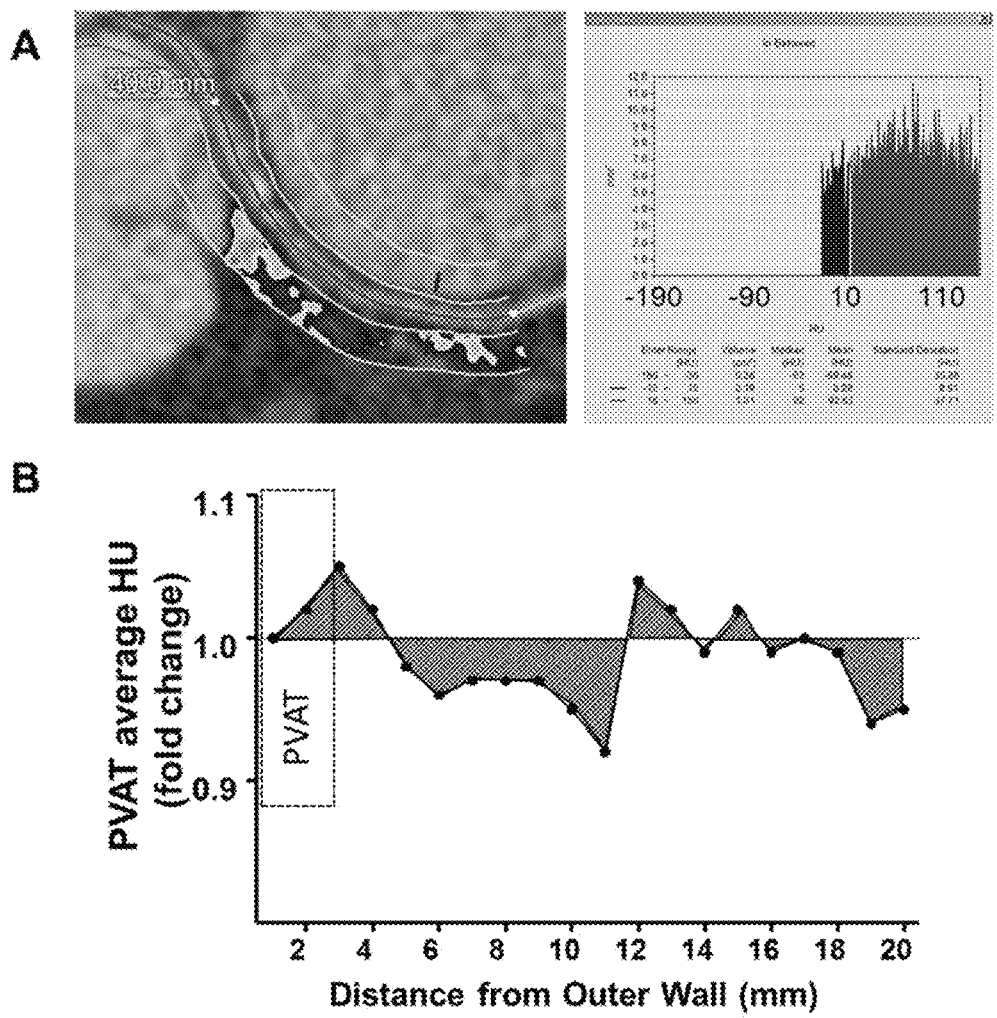
FIG. 10 shows an example of perivascular tissue characterisation around a 40 mm segment of the left circumflex artery with starting point of analysis 1 cm distal to the bifurcation of the left main stem. Voxels corresponding to PVAT (−190HU to −30HU), corresponding to water (−15HU to +15HU) and corresponding to non-adipose tissue (+15 to +120HU) are shown (A). Perivascular tissue was segmented into 1 mm-thick serial concentric layers extending to a 20 mm distance from the outer wall of the artery. PVAT was defined as the adipose tissue lying within a distance equal to the radius of the vessel, and the quantified radiodensity of PVAT in each concentric layer is plotted as fold change compared to baseline radiodensity against the distance from the outer vessel wall (B).
Figure 11:
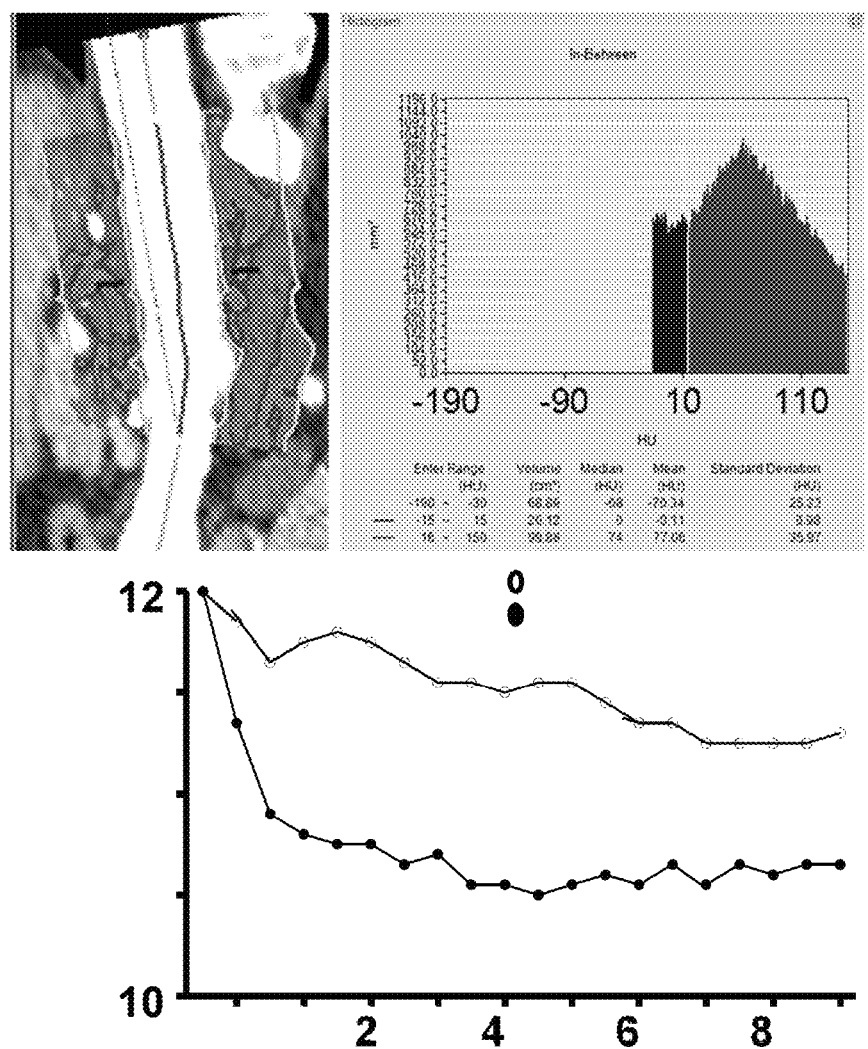
FIG. 11 shows volumetric characterization of peri-aortic adipose tissue around a segment of the abdominal aorta. Perivascular tissue was segmented into 1 mm-thick serial concentric layers extending to a 20 mm distance from the outer wall of the aorta (A). Radiodensity values were calculated for each individual layer and plotted against the distance from the outer wall of a healthy aorta (open circles) and an aortic aneurysm (solid circles). A different pattern of change of radiodensity was seen in the periaortic adipose tissue (expressed as fold changes) in the presence of aortic aneurysm compared to a healthy aorta.

$QR_{PVAT}$, VPCS, VPCI (%) and VPCI-$i_a$ can also be informative for diseases of the aorta (FIG. 10). Both thoracic and abdominal aortae are surrounded by a layer of perivascular adipose tissue that may be involved in the pathogenesis of aortic disease. Detection of early changes in periaortic adipose tissue by using the $QR_{PVAT}$, VPCS, VPCI (%) and VPCI-$i_a$ indices can help identify patients at risk for developing aortic atherosclerosis or even more importantly aortic aneurysms. Moreover, in subjects with diagnosed, stable aortic aneurysms a higher $QR_{PVAT}$, VPCS, VPCI (%) and a lower VPCI-$i_a$ respectively can provide valuable prognostic information about the inflammatory status of the aneurysm and the risk of rupture.

The same analysis can be applied to every vascular bed of the human body, and $QR_{PVAT}$, VPCS, VPCI (%) and VPCI-$i_a$ can be calculated for each individual vessel. FIGS. 7-11 demonstrate such analysis for the right coronary artery, left anterior descending artery, left circumflex artery, aorta and femoral artery.

The invention is further described with reference to the following non-limiting examples:

Example 1

Available computed tomography (CT) images from a 64-slice scanner (General Electric, LightSpeed Ultra, General Electric, Milwaukee, Wis., USA) were used to analyse perivascular tissue and vascular disease phenotype. Acquisition settings were adjusted according to the local clinical protocols to achieve optimum image quality. The reconstructed contrast-enhanced images were transferred to the Aquarius Workstation® from TeraRecon, Inc. (San Mateo, Calif. V.4.4.11) for volume-rendered analysis. 3D curved multiplanar reconstruction was used to define the vascular segment of interest and to analyse perivascular tissue. The reader was required to manually trace a region of interest and perivascular tissue was then segmented in a semi-automated way into concentric layers around the outer vascular wall. Perivascular tissue characteristics were analysed to determine radiodensity values for voxels corresponding to adipose tissue or water within each concentric perivascular layer for the first 20 mm around the outer vascular wall. Mean radiodensity curves for perivascular adipose tissue and water were plotted against the distance from the outer vascular wall to calculate Volumetric Perivascular Characterisation Index (VPCI) and VPCI-integral (VPCI-$i_a$) as described in the description. For analysis of vascular plaque morphology, previously suggested definitions (Obaid et al *Circ Cardiovasc Imaging.* 2013; 6:655-664) were adapted: necrotic core was defined as −1 to +64HU, fibrous plaque as +65 to +260HU and vascular calcification as >600HU.

Example 2

Study Population

Study arm 1 consisted of 453 patients undergoing cardiac surgery at the Oxford University Hospitals NHS Trust (see Table 1). Exclusion criteria were any inflammatory, infectious, liver/renal disease or malignancy. Patients receiving non-steroidal anti-inflammatory drugs were also excluded. During surgery, samples of adipose tissue were harvested, i.e. subcutaneous (ScAT, from the site of the chest incision), thoracic (ThAT, from the central thoracic area, attached to the pericardium) and epicardial adipose tissue (EpAT, from the site of the right atrioventricular groove, away from any visible vessel). Adipose tissue samples were snap-frozen for gene expression studies, histology and CT imaging as explants, as described below. A subgroup of 105 of these patients underwent also CT angiography (CTA), as described below, with an aim to link the histological and biological characteristics of the adipose tissue biopsies, with the imaging characteristics of the same adipose tissue depots in vivo and in vitro.

Study arm 2 included 37 patients undergoing coronary artery bypass grafting surgery (CABG), recruited under the same inclusion/exclusion criteria as study arm 1 (see Table 1). Paired samples of PVAT (adjacent to the proximal RCA) and non-PVAT EpAT (from an area 2 cm away from the RCA, over the right ventricle and not in close proximity with any other coronary arterial branch) were harvested for gene expression studies. In addition, samples of aortic tissue (collected as "buttons" from the site of the anastomosis of bypass grafts on the ascending aorta) were collected and used for ex vivo co-culture experiments with primary adipocytes as described later in this manuscript.

Study arm 3, included a clinical cohort of 273 patients who underwent diagnostic coronary CTA at OUH NHS Trust (156 with and 117 without significant coronary artery disease, see Table 2). This cohort was used to validate the findings generated from study arms 1 and 2 and apply them in a clinical setting.

Blood Sampling and Measurements of Circulating Biomarkers

Venous blood samples were obtained from the patients in Study Arm 1, on the morning before their surgery, after 8 hours of fast. Serum insulin was measured by chemiluminescent microparticle immunoassay and serum glucose by the hexokinase method using commercial kits (ABBOTT, Wiesbaden Germany). Insulin resistance was defined by HOMA-IR, calculated using the formula (glucose×insulin)/405, with glucose measured in mg/dL and insulin in mU/L (Matthews D R, Hosker J P, Rudenski A S, Naylor B A, Treacher D F and Turner R C (1985). Homeostasis model assessment: insulin resistance and beta-cell function from fasting plasma glucose and insulin concentrations in man. *Diabetologia* 28:412-9).

Adipocyte Cell Size Measurement

AT sections, stored at −80° in optimal cutting temperature (OCT) media were cut into 15 micron sections and fixed onto slides. Non-specific antigen binding was blocked using serum-free protein block for 1-2 h (# X0909, Dako Cyto-Mation, Carpinteria, Calif., USA). The staining was developed using the DAB Substrate kit for Peroxidase (# SK-4100, Vector Laboratories, Burlingame, Calif., USA). The slides were mounted with Neo-Mount (#109016, Merck KGaA, Darmstadt, Germany). Cell size was quantified under a bright field microscope. For each patient 3 different fields were quantified per depot using Image J software (V1.48).

RNA Isolation and Quantitative Real Time-Polymerase Chain Reaction (qRT-PCR)

Samples of adipose and aortic tissue were snap frozen in QIAzol (Qiagen, Stanford, Calif.) and stored at −80° C. until processed. RNA was extracted using the RNeasy Micro or Mini kit (Qiagen) and ribonucleic acid was converted into complementary DNA (Quantitect Rev. Transcription kit—Qiagen). The adipose tissue cDNA was then subjected to qPCR using TaqMan probes (Applied Biosystems, Foster City, Calif.) for PPAR-γ (Assay ID: Hs01115513_m1), and cyclophilin as house-keeping gene (Assay ID Hs04194521_s1). Similarly, cDNA derived from aortic tissue was subjected to qPCR using TaqMan probes (Applied Biosystems, Foster City, Calif.) for TNFα (Assay ID Hs01113624_g1), IL6 (Assay ID Hs00985639_m1) and IFNγ (Assay ID Hs00989291_m1), with GAPDH used as house-keeping gene (Assay ID Hs02758991_g1). The reactions were performed in triplicate in 384-well plates, using 5 ng of cDNA per reaction, on an ABI 7900HT Fast Real-Time PCR System (Applied Biosystems). The efficiency of the reaction in each plate was determined based on the slope of the standard curve; expression of each gene of interest relative to its housekeeping gene was calculated using the Pfaffl method (Pfaffl M W (2001). A new mathematical model for relative quantification in real-time RT-PCR. *Nucleic Acids Res* 29:e45).

Effects of Inflammation on Peri-Coronary Primary Pre-Adipocytes Differentiation (Study Arm 2)

To test whether the human arterial wall of patients with advanced atherosclerosis secretes inflammatory mediators able to prevent the differentiation of pre-adipocytes (isolated from PVAT attached on the vascular wall) to mature adipocytes, aortic tissue was harvested from patients undergoing CABG, and cultured in DMEM supplemented with 1% penicillin/streptomycin, 20% FBS. The incubation was done using the tissue explant method (Walton L J, Franklin I J, Bayston T, Brown L C, Greenhalgh R M, Taylor G W and Powell J T (1999). Inhibition of prostaglandin E2 synthesis in abdominal aortic aneurysms: implications for smooth muscle cell viability, inflammatory processes, and the expansion of abdominal aortic aneurysms. *Circulation* 100: 48-54), in the presence/absence of angiotensin II 100 nM for a week to induce additional vascular inflammation. At the same time, pre-adipocytes were isolated from the PVAT attached on the RCA of these patients, by digesting the PVAT for 45 minutes at 37° C. in a solution of collagenase H (1 mg/mL in PBS). The digested tissue was then spun down at 1200 rpm for 5 minutes and re-suspended in DMEM/F-12 supplemented with 10% FBS and 0.25 ng/mL human FGF. Pre-adipocytes and aortic tissue (+/−angiotensin II) were cultured for 1 week separately. At the end of the week, the aortic tissue was washed to remove angiotensin II and co-cultured with the isolated primary pre-adipocytes. When the pre-adipocytes were confluent around the aortic tissue, they were differentiated in DMEM/F12 supplemented with 0.5 mM 3-isobutyl-1-methylxanthine (IBMX), 100 nM insulin, 100 nM dexamethasone, 2 nM triiodo-L-thyronine (T3), 10 µg/ml transferrin, 1 µM rosiglitazone, 33 µM biotin and 17 µM pantothenic acid, 3% FBS for 7 days followed by adipocytes maintaining media containing DMEM/F12 with 10 nM insulin, 10 nM dexamethasone for 2 days (Lee M J, Wu Y and Fried S K (2012). A modified protocol to maximize differentiation of human preadipocytes and improve metabolic phenotypes. *Obesity (Silver Spring)* 20:2334-40). The adipocytes were monitored for cell size and lipid accumulation visually and by staining with oil-red O followed by quantification using Image J (version 1.48) at day 9. In parallel experiments, the ability of aortic tissue to express inflammatory cytokines (e.g. IL6, TNF-α or IFN-γ that could then exert a paracrine effect on PVAT), was tested by quantifying the expression of these cytokines in aortic tissue biopsies using RTPCR, after 7 days culture with/without angiotensin II 100 nM.

Effects of Inflammation on Peri-Coronary Pre-Adipocyte Differentiation (Study Arm 2)

The direct effect of vascular inflammation on perivascular adipocyte differentiation capacity was tested by incubating primary pre-adipocytes isolated from PVAT of patients undergoing CABG with recombinant TNF-α (4 ng/ml), IL-6 (25 ng/ml) and IFN-γ (20 ng/ml), during a differentiation time course induced by DMEM/F12 with 0.5 mM IBMX, 100 nM insulin, 100 nM dexamethasone, 2 nM T3, 10 µg/ml transferrin, 1 µM rosiglitazone, 33 µM biotin and 17 µM pantothenic acid, 3% FBS for 7 days followed by adipocytes maintaining media containing DMEM/F12 with 10 nM insulin, 10 nM dexamethasone for 2 days. For the differentiation time course, images were taken every 3 days and RNA was isolated. The degree of differentiation of the pre-adipocytes was estimated by a) the changes in adipocyte morphology and size b) the accumulation of lipid droplets (stained using oil-red-o) c) the expression of adipocyte differentiation genes, i.e. PPAR-γ, an early phase differentiation marker, CEBPA CCAAT/enhancer binding protein (C/EBP) alpha (CEBPA), a late phase differentiation marker, and fatty acid binding protein-4 (FABP4), a marker of terminal adipocyte differentiation/mature adipocytes.

Effects of Inflammation on Peri-Coronary Pre-Adipocyte Proliferation (Study Arm 2)

Human pre-adipocytes isolated from PVAT (peri-coronary AT) were cultured in 96 well plates ($5 \times 10^3$ cells per well) for 24 h. Then paired wells were treated with/without TNF-α (4 ng/ml), IL-6 (25 ng/ml), and IFN-γ (20 ng/ml) for 24 h and 48 h. A 20 µL CellTiter 96 AQueous One Solution Reagent (Promega) was added to each well and the plates were incubated for 2 h at 37° C. Subsequently, absorbance at 490 nm was measured using a 96-well plate reader.

Oil-Red O Staining

Briefly a stock solution of oil-red O has been prepared dissolving 0.3 g of oil-red O (Sigma Aldrich) with 100 mL of isopropanol. At day 9 of the differentiation time course, adipocytes were washed twice with PBS and fixed with paraformaldehyde 4% for 10 minutes at room temperature. Cells were rinsed with distilled water followed by a 5 minutes wash with 60% isopropanol. Cells then were stained for 10 minutes with a solution of oil-red O (3 parts of oil-red O stock solution/2 parts of water) and finally washed with tap water. Nuclei were counterstained with a solution of hematoxylin. Formation of lipid droplets was observed by phase contrast microscopy. To quantify to amount of lipid droplets accumulated in mature adipocytes, cells stained with oil-red O were washed with a solution of 60% isopropanol in order to extract the oil-red O. The absorbance of the dye was quantified spectrophotometrically, at 500 nm. For the co-culture experiments of adipocytes with aortic tissue, quantification of oil-red-O was performed using image analysis of the fixed slides using Image J (version 1.48) rather than spectrophotometrically, to avoid the quantification bias derived from the fact that adipocytes do not grow under the aortic tissue samples, leading to a variable surface area of growing adipocytes per well.

Computerised Tomography Studies (Study Arms 1 and 3)

Participants in study arms 1 and 3 underwent a Cardiac CT scan on a 64-slice scanner (General Electric, LightSpeed Ultra, General Electric, Milwaukee, Wis., USA). The medial antecubital vein was cannulated with a 21-gauge needle. Heart rate was reduced below 60 bpm by intravenous injection of beta-blockers (mean dose of 40 mg metoprolol IV). Sublingual glyceryl-trinitrate (800 ug) was also administered to achieve maximum coronary vasodilatation immediately before the scan. Participants firstly underwent a non-contrast CT scan (0.35 sec rotation time, 2.5 mm axial slice thickness, 20 mm detector coverage, 20 mm interval, tube energy of 120 kVp and 200 mA). The carina was used as the cranial landmark, while diaphragm as the caudal one. Lung field of view was extended to cover the whole thoracic soft tissue (for subcutaneous adipose tissue analysis). By using the same landmarks, a coronary CT angiography scan followed by intravenous injection of 95 mL of iodine-based contrast medium (Niopam 370, BRACCO UK Ltd) at a high rate (5 mL/sec) and there was a flush of 50 mL normal saline 0.9%. CT scanning was initiated as soon as contrast-medium filled the ascending aorta. Tube energy of 120 kVp was used in all participants (axial slice thickness of 0.625 mm, rotation time of 0.35 sec, detector coverage of 40 mm, a 40% dose reduction protocol for mA, and reference mA adjusted for body size). Prospective image acquisition was used by ECG-gating at the 70% of cardiac cycle (with 100 msec padding for optimal imaging of the right coronary artery if required). Participants with step artefacts on acquisition or sub-optimal RCA imaging were excluded from any analyses.

Adipose Tissue Characterization by CT:

The reconstructed images were transferred to the Aquarius Workstation® V.4.4.11 (TeraRecon, Inc., Foster City, Calif., U.S.A) for volume-rendered analysis. AT was defined as all voxels within the −190 to −30HU window. The voxel radiodensity histograms were blotted and the quantified radiodensity index (QR) was defined as the average voxel radiodensity of the AT volume of interest (within the pre-specified window of −190 to −30 HU) in 3 dimensions. The working hypothesis was that the adipocyte size is the main driver of QR (as higher proportion of lipid phase (adipocytes) to aqueous phase (extracellular space), and larger adipocytes would lead to more negative QR. The EpAT was tracked by contouring of the pericardial sac in a semi-automated way (starting from the bifurcation of the pulmonary artery at the most cranial point up to the apex of the heart at the most caudal point). ScAT was tracked by sampling of all thoracic subcutaneous AT, at the height of the sternal end and extending cranially for a total of 25 mm. QR was calculated in EpAT and ScAT from the 3D reconstructed images using a research version of Aquarius Software (TeraRecon, Inc., V.4.4.11), developed in the context of the current research programme. Patient scans in Study Arm 1 were performed both with and without a contrast agent, to access the impact of the contrast agent on the absolute values of QR measured.

Peri-Coronary Adipose Tissue Characterization:

3D curved multiplanar reconstruction was used to define the vascular segment of interest and to analyse perivascular tissue. The right coronary artery (RCA) was used to perform pericoronary adipose tissue imaging, since this coronary artery has no major branches and PVAT/non-PVAT can be easily defined. The first 1 cm of the proximal RCA was omitted from analysis to exclude adipose tissue lying close to the coronary ostium/aortic root from analysis. Then a 4 cm-long segment of the RCA ($10^{th}$ to $50^{th}$ mm from right coronary ostium) was tracked in an automated-way. Inner and outer layers of analysis were manually adjusted to track lumen and outer wall boundaries respectively. Then perivascular tissue was segmented in a semi-automated way into 20 concentric cylindrical 1 mm-thick layers around the outer vascular wall. QR was calculated for each of the twenty layers of tissue. Average radiodensity curves of AT were plotted against the radial distance from the outer vascular wall.

QR in PVAT:

There is no clear biological definition of PVAT, so for the imaging studies PVAT was defined as the adipose tissue radiodensity in a layer of tissue within a radial distance from outer coronary artery wall equal to the average diameter of the tracked RCA segment. Non-PVAT radiodensity was defined at the most distal concentric layer of AT from RCA wall. Volumetric Perivascular Characterisation Index (VPCI) was then calculated as the difference of QR in PVAT from QR in non-PVAT (2 cm away from the RCA's outer wall), as defined above.

Coronary Calcium Score:

Coronary calcium score (CCS) was measured on Aquarius Workstation® for all coronaries and for RCA separately, by calculating Agatston score (Agatston A S, Janowitz W R, Hildner F J, Zusmer N R, Viamonte M, Jr. and Detrano R (1990). Quantification of coronary artery calcium using ultrafast computed tomography. *J Am Coll Cardiol* 15:827-32).

Coronary Plaque Analysis Using CTA:

For analysis of vascular plaque morphology, previously suggested HU thresholds (Obaid D R, Calvert P A, Gopalan D, Parker R A, Hoole S P, West N E, Goddard M, Rudd J H and Bennett M R (2013). Atherosclerotic plaque composition and classification identified by coronary computed tomography: assessment of computed tomography-generated plaque maps compared with virtual histology intravascular ultrasound and histology. *Circ Cardiovasc Imaging* 6:655-64) were adapted. HU mapping of the right coronary artery wall was used to quantify fibrous plaque volume (65 to 265HU). Fibrous plaque index was calculated as the ratio of fibrous plaque volume to total vessel volume.

CT Scans of Adipose Tissue Explants

Frozen samples of ScAT, ThAT and EpAT tissue from all patients in study arm 1 were scanned while frozen on dry ice, to evaluate the ability of QR to describe the adipose tissue biology. Adipose tissue explants were scanned on a Toshiba Aquilion One 320-slice CT scanner, using dual energy helical acquisition with 135 keV and 80 keV, 50 mA, 0.5 sec rotation time, 0.5 mm slice thickness, and image reconstruction at 120 keV for the QR analysis. In 105 of these patients paired CT scans were performed (in vivo scans as well as scans of tissue explants from the same anatomical sites/depots), to validate the in vitro CT imaging model against in vivo imaging, and to allow use of this model to understand the biological value of QR in the study of human AT.

Statistical Analysis

Continuous variables were tested for normal distribution using the Kolmogorov-Smirnov test. Non-normally distributed variables were log-transformed for analysis and are presented as median [$25^{th}$-$75^{th}$ percentile]. Normally distributed variables are presented as mean±SEM.

Figure 4:
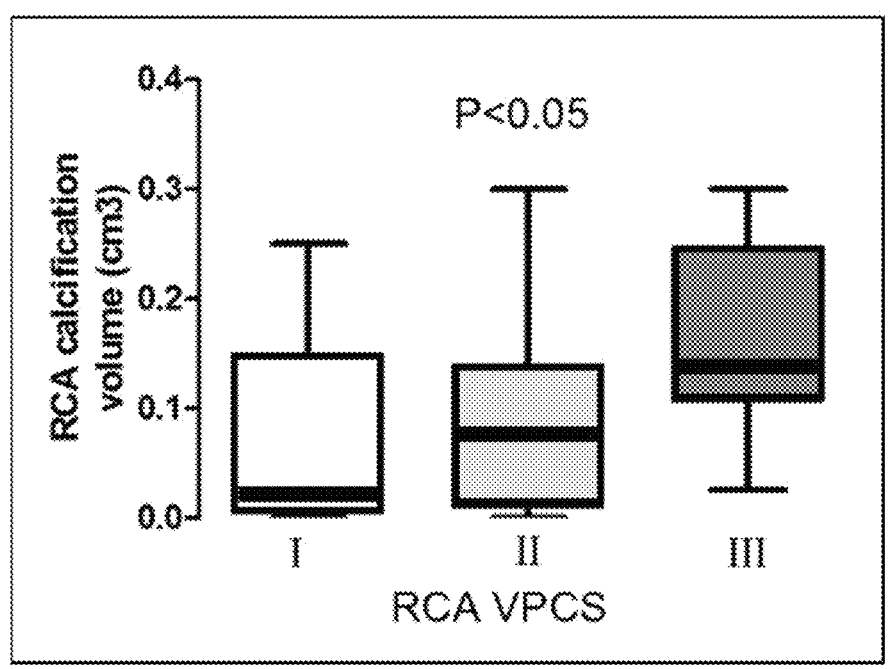
FIG. 4 shows the association between the volumetric perivascular characterisation score (VPCS) and coronary calcification. Coronary vessels with higher VPCS were associated with increased coronary artery wall calcification volume. Calcium was defined as all voxels of the vascular wall with HU values >600. P-value for One-way ANOVA after Bonferroni correction for comparisons between three groups. (I<2, II: 2-8, III>8).
Figure 5:
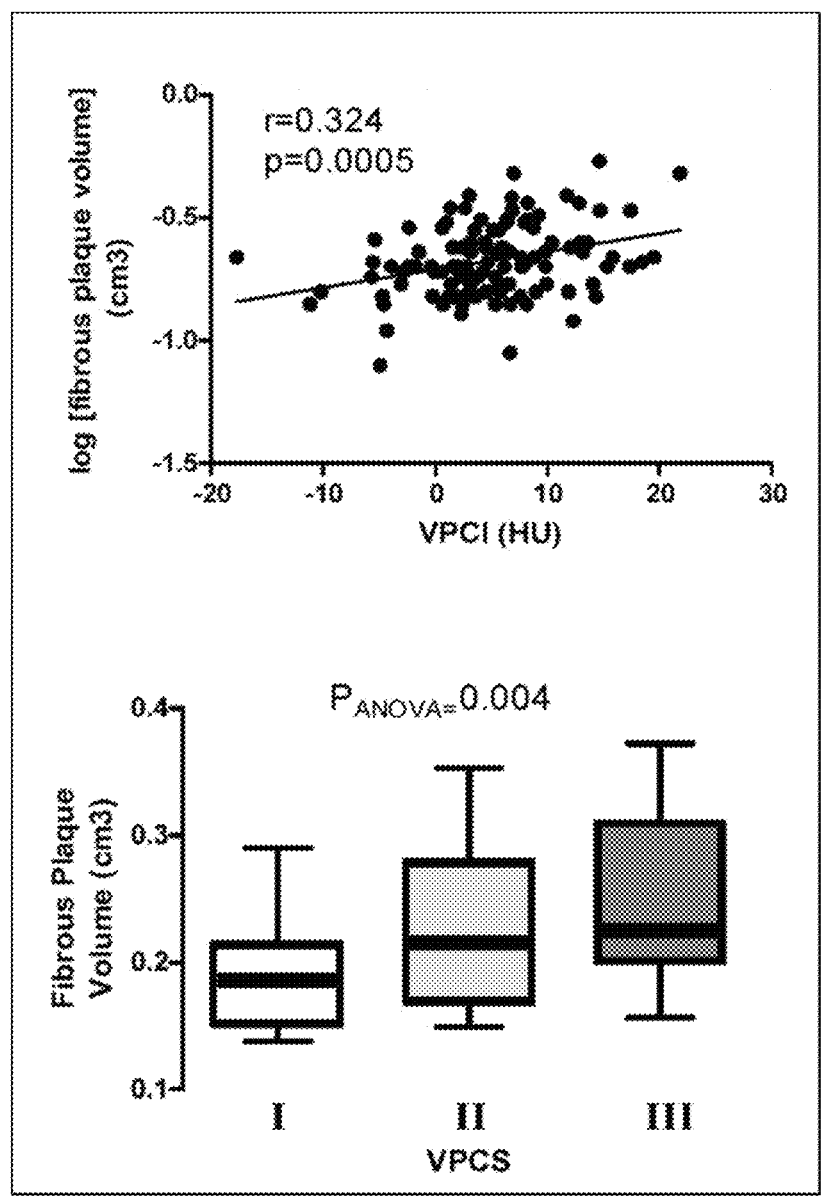
FIG. 5 shows that VPCI as a continuous variable and VPCS as a categorical variable (I<2 II: 2-8, III>8) were significantly related with the total volume of fibrous plaque in the underlying coronary artery. Fibrous plaque was defined as those voxels of vascular wall with quantified radiodensity values between 65 and 260 HU.
Figure 6:
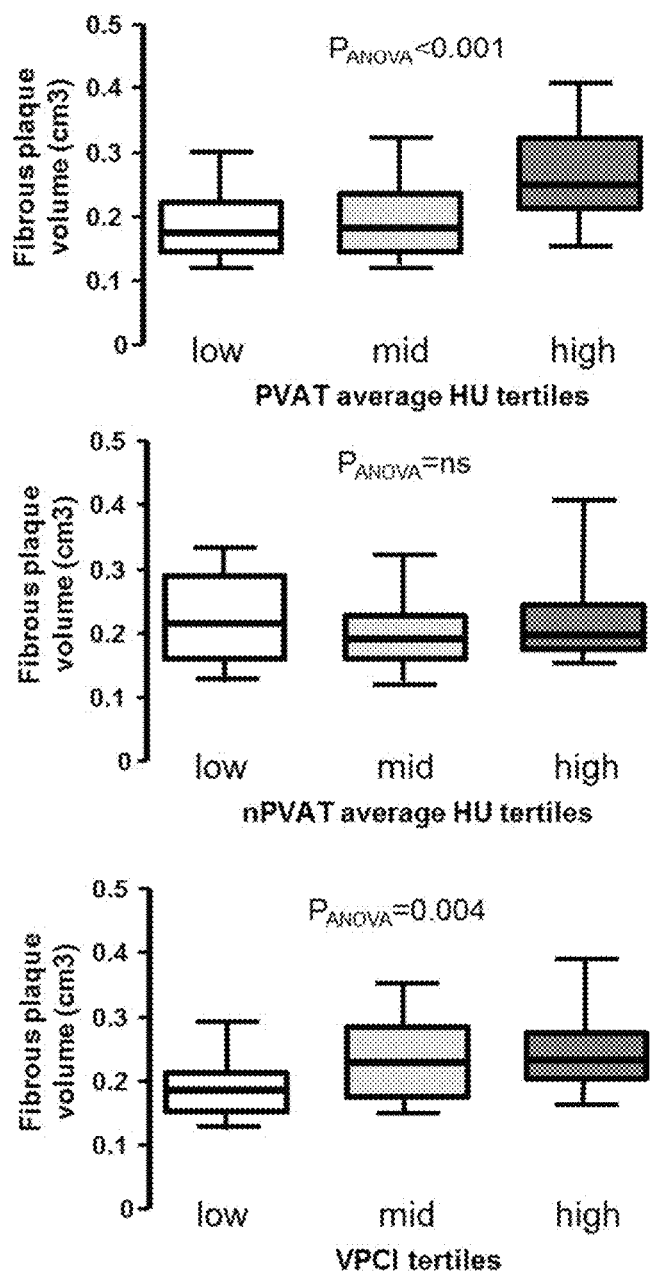
FIG. 6 shows associations between the perivascular adipose tissue and plaque characteristics in patients with coronary artery disease. Forty two coronary patients were scanned by coronary CT angiography as part of the AdipoRedOx study. There was a striking positive association between the volume of fibrous plaque and the density of PVAT (A) but not of non-PVAT (B), indicating that PVAT changes closer to human arteries are associated with a higher volume of fibrous plaque. The difference in the densities of PVAT and non-PVAT (VPCI) was a predictor of coronary fibrous plaque volume (C). Necrotic core was defined as those voxels of vascular wall with radiodensity values between −1 and 64 HU, fibrous plaque was defined as those voxels of vascular wall with radiodensity values between 65 and 260 HU and calcium was defined as all voxels of the vascular wall with radiodensity values >600 HU. P-values are derived from ANOVA after Bonferroni correction for comparisons between 3 groups.
Figure 7:
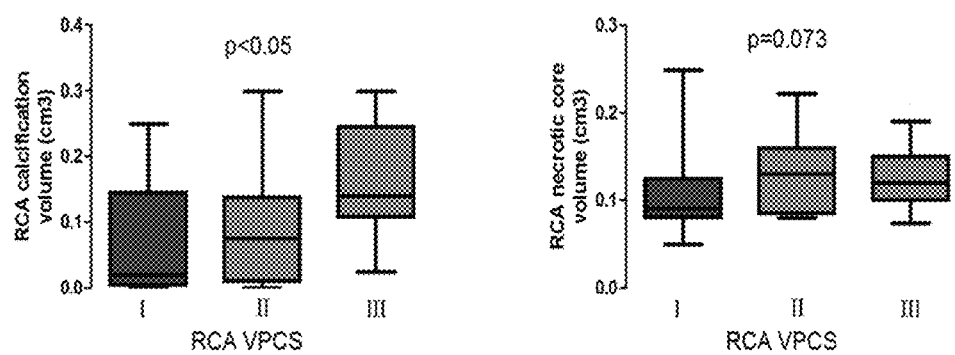
FIG. 7 shows associations between volumetric perivascular tissue characterisation score values and plaque characteristics in patients with coronary artery disease. Coronary CT angiography was carried out on forty two coronary patients as part of the AdipoRedOx study. Volumetric perivascular characterisation score (VPCS) along with necrotic core volume and artery wall calcification volume of the right coronary artery were calculated in the contrast-enhanced CT images. There was a positive association between the VPCS and extend of coronary artery wall calcification (A). There was also a trend towards higher volume of necrotic core with higher VPCS, although this did not reach statistical significance (B). Necrotic core was defined as those voxels of vascular wall with radiodensity values between −1 and 64 HU, and calcium as all voxels of the vascular wall with radiodensity values >600 HU. P-values are derived from Kruskal Wallis for comparisons between 3 groups.
Figure 8:
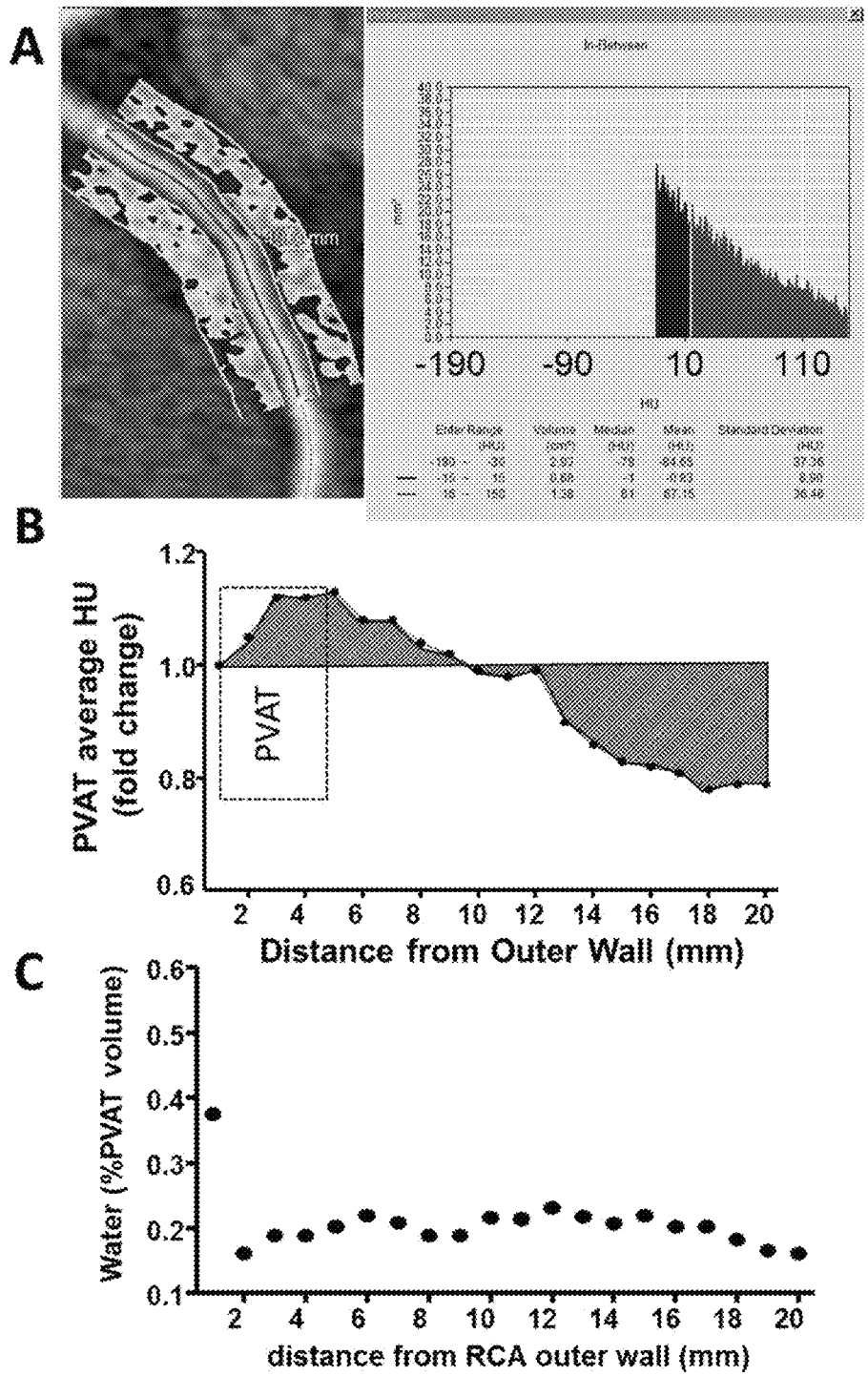
FIG. 8 shows perivascular tissue characterisation around a 40 mm segment of the right coronary artery (starting point of analysis 1 cm distal to the right ostium). Voxels corresponding to perivascular adipose tissue (PVAT, −190HU to −30HU), corresponding to water (−15HU to +15HU) and corresponding to non-adiopse tissue (+15 to +120HU) are shown. Perivascular tissue was segmented into 1 mm-thick serial concentric layers extending up to a 20 mm distance from the outer wall of the artery. The quantified radiodensity of PVAT in each concentric layer is plotted as fold change compared to baseline radiodensity against the distance from the outer vessel wall (B). Based on the radius of the vessel, PVAT is distinguished from non-PVAT (nPVAT) and the volumetric perivascular characterization indices are calculated. The area under curve (AUC, grey shaded area) divided by the quantified radiodensity for PVAT gives the VPCI-i$_a$ index, while the difference between the quantified radiodensity for PVAT and the quantified radiodensity for nPVAT is the VPCS index. The plot of the water content of perivascular tissue (expressed as % volume of PVAT volume in each concentric layer, C) can be also used to assess the water content of perivascular tissue, as a secondary index of perivascular tissue inflammation.
Figure 9:
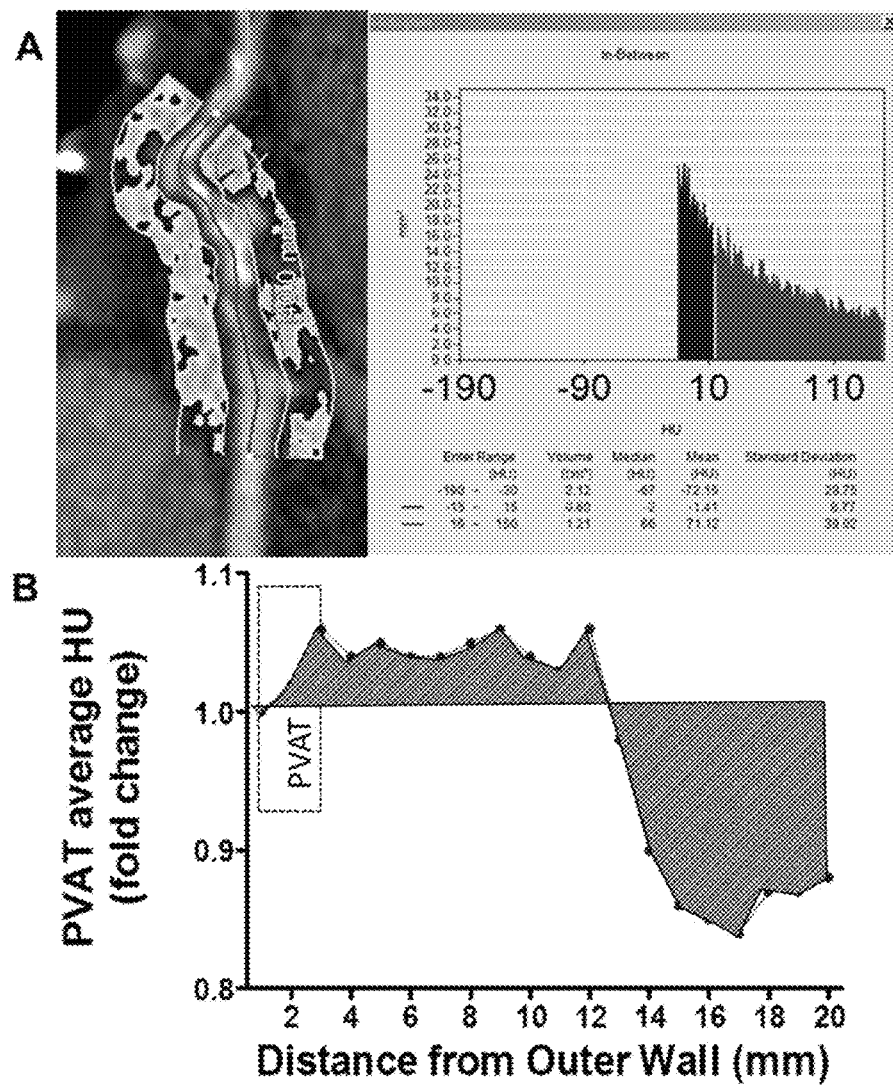
FIG. 9 shows an example of perivascular tissue characterisation around a 40 mm segment of the left anterior descending artery with starting point of analysis 1 cm distal to the bifurcation of the left main stem. Voxels corresponding to PVAT (−190HU to −30HU), corresponding to water (−15HU to +15HU) and corresponding to non-adipose tissue (+15 to +120HU) are shown (A). Perivascular tissue was segmented into 1 mm-thick serial concentric layers extending up to a 20 mm distance from the outer wall of the artery. PVAT was defined as the adipose tissue lying within a distance equal to the radius of the vessel, and the quantified radiodensity of PVAT in each concentric layer is plotted as fold change compared to baseline radiodensity against the distance from the outer vessel wall (B).

Comparisons of characteristics between different groups of patients were performed using unpaired t-test for 2 groups or one-way ANOVA for 3 groups. For comparisons of the differences in adipocyte size and the expression of specific genes in paired PVAT and non-PVAT in FIG. 4, Wilcoxon paired rank test was used. The between groups differences in the QR change over the distance from RCA (FIG. 11), was studied using two way ANOVA for repeated measures, with (distance from RCA outer wall).times.(group) interaction. For between-group differences in the adipocyte differentiation time-courses we used two way ANOVA for repeated measures, with (time).times.(group) interaction.

Categorical variables were compared by using chi-square test, as appropriate. Correlations between continuous variables were assessed by using bivariate analysis, and Pearson's r or Spearman's rho coefficient was estimated as appropriate. All statistical tests were performed using SPSS v20.0 and P<0.05 was considered statistically significant.

TABLE 1

Demographic characteristics of study participants

| | Study arm 1 | | Study arm 2 (ex vivo studies) |
|---|---|---|---|
| | All (CT AT explants) | CCTA (in vivo) | |
| Participants (n) | 453 | 105 | 37 |
| Age (years) | 66.8 ± 0.49 | 65.0 ± 0.97 | 65.4 ± 1.54 |
| Male gender (%) | 80.8 | 86.9 | 78.4 |
| Hypertension (%) | 70.9 | 74.8 | 70.3 |
| Hyperlipidaemia (%) | 75.5 | 88.8 | 86.5 |
| Type 2 diabetes (%) | 24.1 | 28.2 | 13.5 |
| Smoking (ex/active) (%) | 53.0/11.3 | 51.4/12.1 | 62.2/5.4 |
| BMI (Kg/m$^2$) | 28.4 ± 0.2 | 28.7 ± 0.4 | 29.21 ± 0.7 |
| Cholesterol (mg/dl) | 4.35 ± 0.18 | 5.2 ± 0.5 | 185.6 ± 12.8 |
| Glucose (mg/dl) | 111.8 ± 2.16 | 113.9 ± 4.6 | 98.3 ± 10.2 |
| Insulin (μU/ml) | 11.0 ± 1.5 | 11.5 ± 2.9 | 6.8 ± 1.1 |
| HOMA-IR | 3.67 ± 0.63 | 3.5 ± 1.4 | 1.95 ± 0.5 |
| HDL (mg/dl) | 1.19 ± 0.06 | 1.08 ± 0.06 | 50.27 ± 4.8 |
| Medication (%) | | | |
| ACEi | 48.5 | 45.8 | 40.5 |
| ARBs | 14.3 | 17.8 | 13.5 |
| Beta blockers | 64.8 | 74.8 | 75.7 |
| Aspirin/Clopidogrel | 79.2/24.0 | 86.0/37.4 | 86.5/27.0 |
| Statins | 80.8 | 86.9 | 83.8 |
| CCBs | 26.8 | 31.8 | 18.9 |

CCTA: Coronary Computerised tomography angiography;
CAD: Coronary artery disease;
ACEi: Angiotensin converting enzyme inhibitors;
ARBs: Angiotensin receptor blockers;
CCBs: Calcium channel blockers.
HOMA-IR: Homeostatic model of insulin resistance;
HDL: High density lipoprotein;
BMI: Body mass index

TABLE 2

Demographic characteristics of study participants in study arm 3

| | Study arm 3 | |
|---|---|---|
| | No CAD | CAD |
| Participants (n) | 117 | 156 |
| Age (years) | 58.6 ± 1.0 | 64.5 ± 0.8* |
| Male gender (%) | 51.3 | 8.3.* |
| Hypertension (%) | 33.0 | 71.1* |
| Hyperlipidaemia (%) | 25.5 | 78.2* |
| Type 2 diabetes (%) | 8.5 | 29.4* |
| Smoking (ex/active) (%) | 21.6/1.9 | 42.3/9.9* |
| BMI (Kg/m$^2$) | 29.5 ± 2.3 | 28.7 ± 0.5 |
| Medication (%) | | |
| ACEi | 5.1 | 37.8* |
| ARBs | 3.4 | 14.7* |
| Beta blockers | 16.2 | 62.2* |
| Aspirin/Clopidogrel | 16.7/0 | 78.4/26.3* |
| Statins | 17.9 | 77.7* |
| CCBs | 7.7 | 24.4* |

CAD: Coronary artery disease;
ACEi: Angiotensin converting enzyme inhibitors;
ARBs: Angiotensin receptor blockers;
CCBs: Calcium channel blockers.
BMI: Body mass index;
$P < 0.01$ vs. no CAD Results Characterizing Adipocyte Differentiation Status and Cell Size in Different Adipose Tissue Depots We first studied the phenotypic differences between EpAT, ThAT and ScAT obtained from 453 patients undergoing cardiac surgery (Study arm 1, Table 1). EpAT and ThAT had significantly smaller adipocytes compared to ScAT, reflecting poor differentiation of pre-adipocytes to large mature adipocytes (FIG. 13A-D**). Indeed, the poor adipocyte differentiation status in EpAT/ThAT compared to ScAT, was documented by the significantly lower expression of PPAR-γ (characterizing early stages of adipocyte differentiation (Ntambi J M and Young-Cheul K (2000). Adipocyte differentiation and gene expression. *J Nutr* 130:3122S-3126S), FIG. 13E), CEBPA (characterizing late stage of adipocyte differentiation (Ntambi J M and Young-Cheul K (2000). Adipocyte differentiation and gene expression. *J Nutr* 130:3122S-3126S), FIG. 13F) and FABP4 (expressed only in large, mature adipocytes, (Ntambi J M and Young-Cheul K (2000). Adipocyte differentiation and gene expression. *J Nutr* 130:3122S-3126S) FIG. 13G). So the expression of these adipocyte differentiation markers in adipose tissue could be used as a marker of the average adipocyte size.

Figure 14:
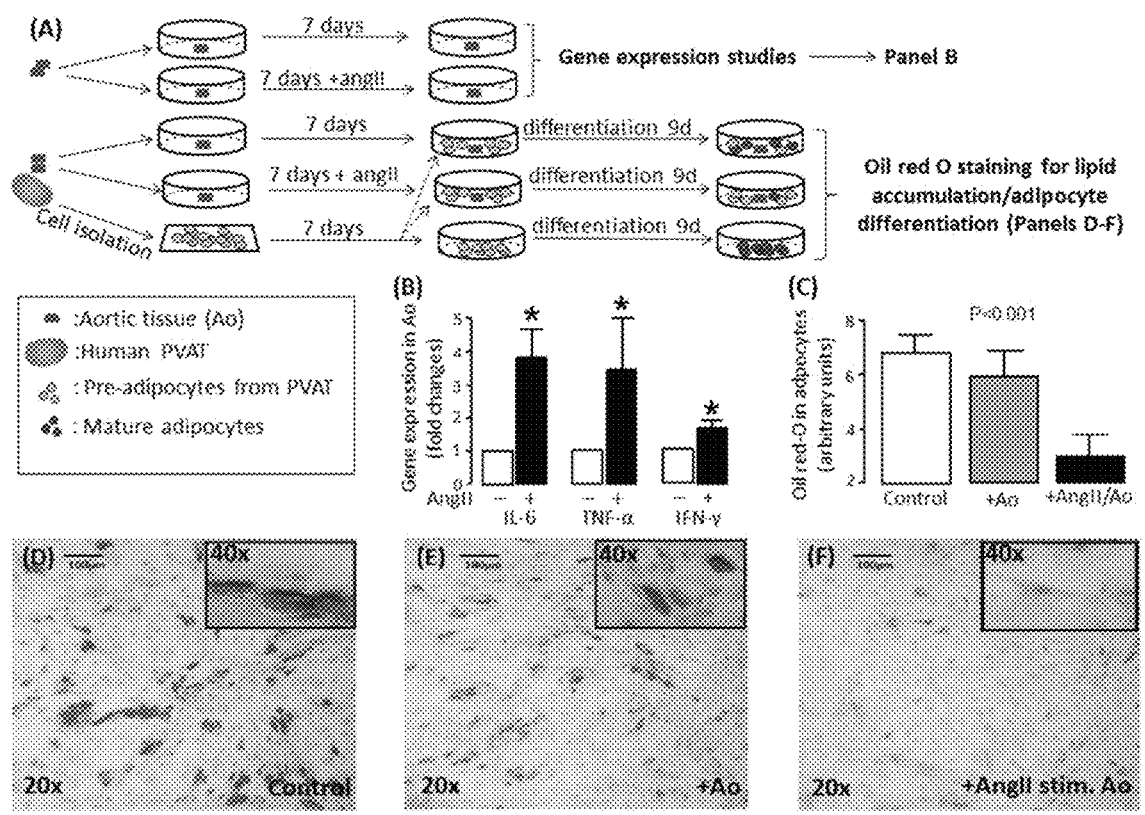
FIG. 14A shows experimental design of co-culture experiments in study arm 2 in which human aortic tissue (Ao) from 15 patients undergoing coronary artery bypass grafting was harvested and cultured for 7 days+/−angiotensin II (AngII) 100 nM. Pre-adipocytes isolated from perivascular adipose tissue (PVAT) around the RCA were also cultured for this period. A week later, the Ao was washed to remove angiotensin II (Ang II) and was co-cultured with the pre-adipocytes. Then a differentiation time-course was induced.
FIG. 14B shows that Ang II induced the expression of inflammatory cytokines in the Ao (i.e. interleukin 6 (IL-6), tumor necrosis factor alpha (TNF-α) and interferon gamma (IFN-γ)).
FIG. 14C-F shows that co-culture of pre-adipocytes with Ang II pre-stimulated Ao prevented the differentiation of the pre-adipocytes to mature adipocytes, as demonstrated by the lack of lipid droplets in these adipocytes by differentiation day 9 compared to pre-adipocytes differentiated without Ao. *P<0.05 vs control.

Effects of Vascular Inflammation on the Differentiation Status of Adipocytes in Human Peri-Coronary Adipose Tissue Given our recent studies in humans (Margaritis M, Antonopoulos A S, Digby J, Lee R, Reilly S, Coutinho P, Shirodaria C, Sayeed R, Petrou M, De Silva R, Jalilzadeh S, Demosthenous M, Bakogiannis C, Tousoulis D, Stefanadis C, Choudhury R P, Casadei B, Channon K M and Antoniades C (2013). Interactions between vascular wall and perivascular adipose tissue reveal novel roles for adiponectin in the regulation of endothelial nitric oxide synthase function in human vessels. *Circulation* 127:2209-21, and Antonopoulos A S, Margaritis M, Coutinho P, Shirodaria C, Psarros C, Herdman L, Sanna F, De Silva R, Petrou M, Sayeed R, Krasopoulos G, Lee R, Digby J, Reilly S, Bakogiannis C, Tousoulis D, Kessler B, Casadei B, Channon K M and Antoniades C (2014). Adiponectin As A Link Between Type 2 Diabetes Mellitus And Vascular NADPH-Oxidase Activity In The Human Arterial Wall: The Regulatory Role Of Perivascular Adipose Tissue. *Diabetes* 64(6): 2207-19) and additional evidence from animal studies (Takaoka M, Suzuki H, Shioda S, Sekikawa K, Saito Y, Nagai R and Sata M (2010). Endovascular injury induces rapid phenotypic changes in perivascular adipose tissue. *Arterioscler Thromb Vasc Biol* 30:1576-82) suggesting that adipocytes in PVAT "sense" pro-atherogenic processes happening in the underlying vascular wall modifying their biology, we assumed that inflammatory signals from the human arterial wall may be diffused to the perivascular adipose tissue affecting local adipocyte differentiation status and size. As samples of human coronary artery can't be obtained for research, we used aortic tissue harvested during CABG surgery (aortic "buttons" obtained from the point of graft anastomosis on the ascending aorta from patients in study arm 2, Table 1) as our model system, which we cultured ex vivo for a week in the presence or absence of angiotensin II (to induce further vascular inflammation) (FIG. 14A) (Walton L J, Franklin I J, Bayston T, Brown L C, Greenhalgh R M, Taylor G W and Powell J T (1999). Inhibition of prostaglandin E2 synthesis in abdominal aortic aneurysms: implications for smooth muscle cell viability, inflammatory processes, and the expansion of abdominal aortic aneurysms. *Circulation* 100:48-54). At the end of this week, treatment with angiotensin II was able to up-regulate the expression of inflammatory cytokines IL-6, TNF-α and IFN-γ in the aortic tissue (FIG. 14B). After this first week in culture, we washed the aortic tissue to remove angiotensin II and co-cultured it with the pre-adipocytes collected from the same patient, followed by induction of adipocyte differentiation to mature adipocytes using well established methodology (Adams M, Montague C T, Prins J B, Holder J C, Smith S A, Sanders L, Digby J E, Sewter C P, Lazar M A, Chatterjee V K and O'Rahilly S (1997). Activators of peroxisome proliferator-activated receptor gamma have depot-specific effects on human preadipocyte differentiation. *J Clin Invest* 100:3149-53). We observed that adipocytes cultured with aortic tissue pre-treated with angiotensin II had slower differentiation to mature adipocytes compared to pre-adipocytes cultured in the absence of aortic tissue, while pre-adipocytes co-cultured with un-stimulated aortic tissue had an intermediate differentiation status (FIG. 14), suggesting that mediators released from the "inflamed" human vascular wall can exert paracrine effects on the neighbouring PVAT preventing the differentiation of pre-adipocytes to mature adipocytes.

Figure 16:
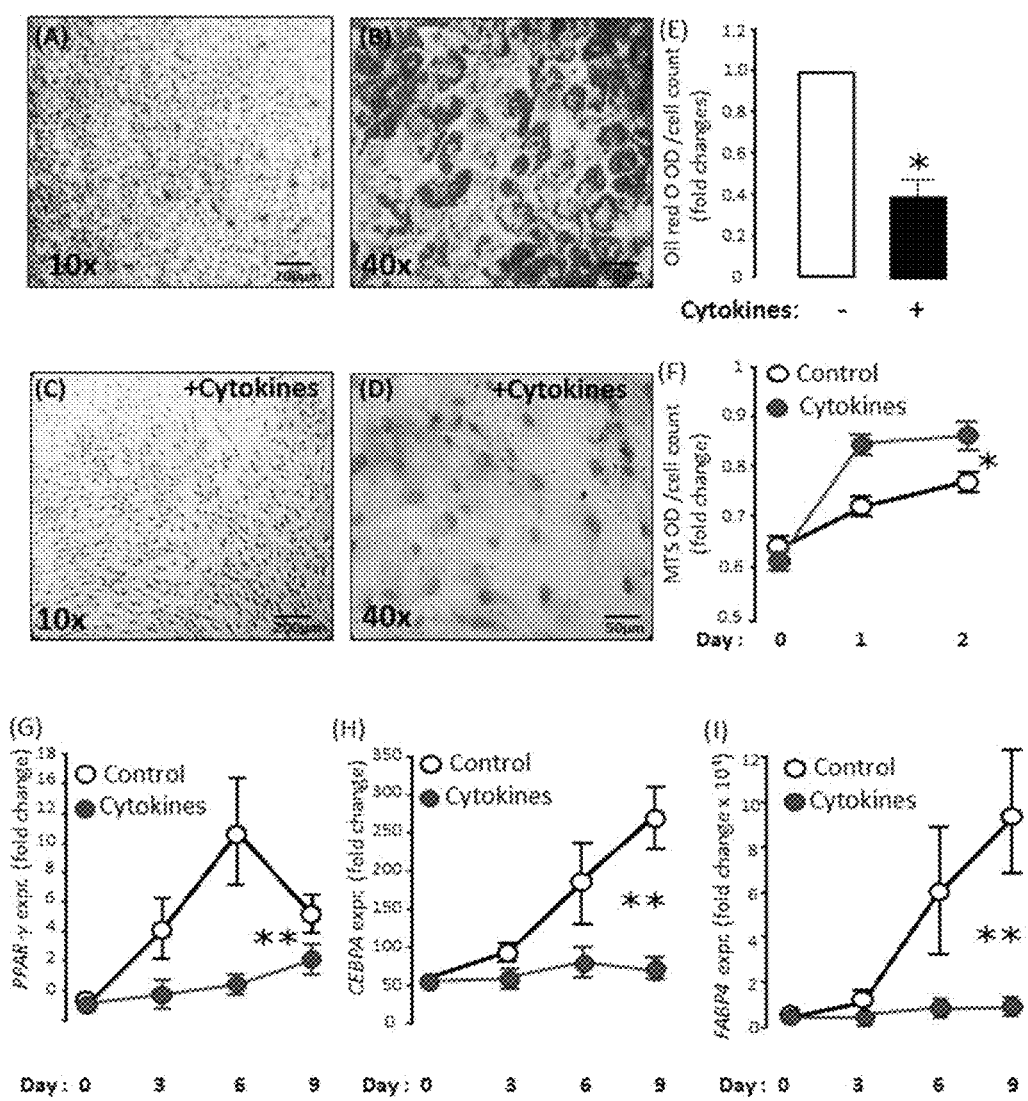
FIG. 16 shows the effect of cytokines on differentiation of human pre-adipocytes isolated from perivascular adipose tissue (PVAT) around the right coronary artery and differentiated in the presence or absence of inflammatory cytokines (recombinant TNF-α (4 ng/ml), IL-6 (25 ng/ml) and IFN-γ (20 ng/ml)).
Figure 19:
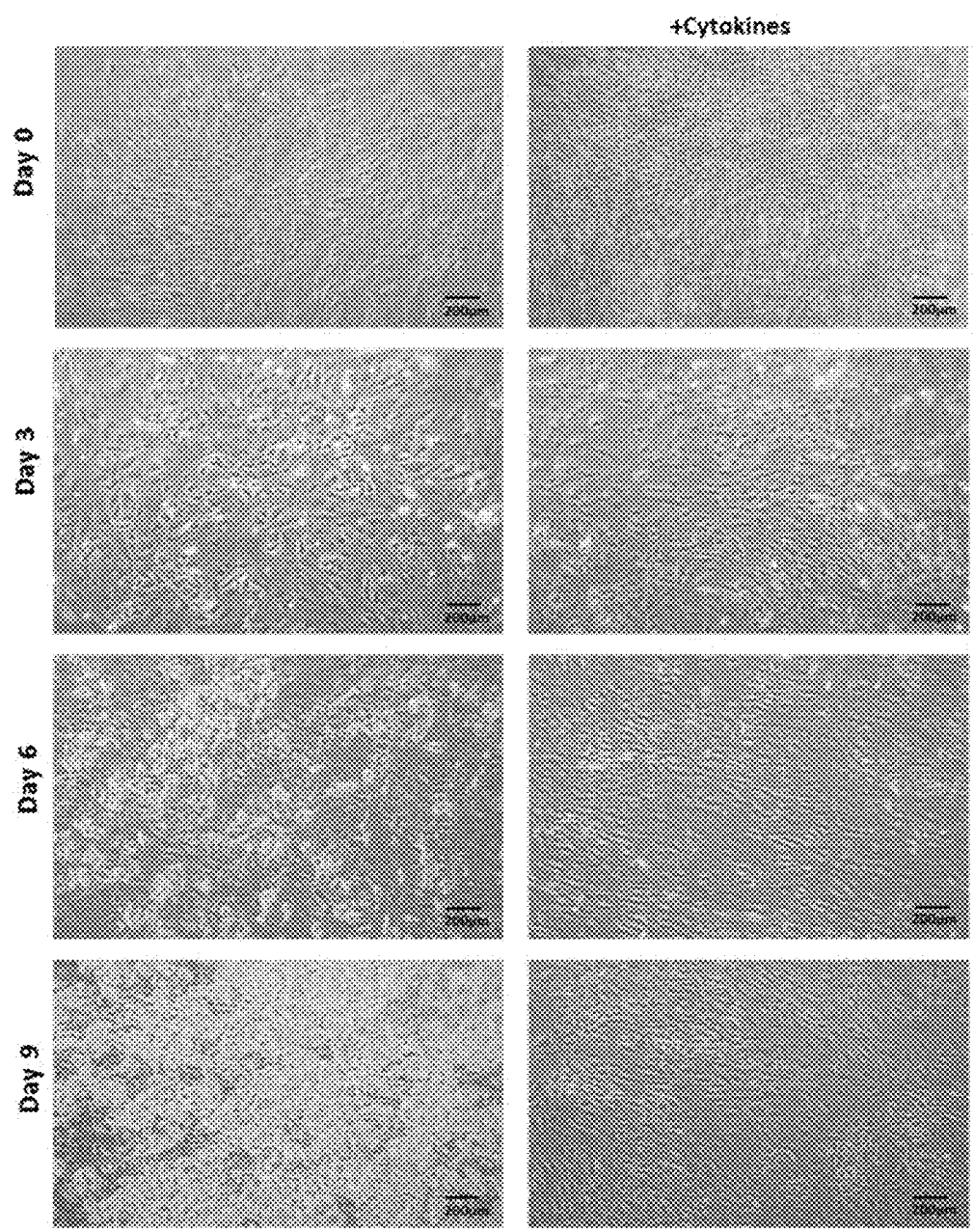
FIG. 19 shows the effect of proinflammatory cytokines on adipocyte differentiation in vitro. Human pre-adipocytes were isolated from peri-coronary adipose tissue harvested from patients undergoing coronary artery bypass grafting surgery, and differentiated to adipocytes in the presence or absence of proinflammatory cytokines: interleukin-6 (2 ng/ml), tumour necrosis factor-alpha (4 ng/ml) and interferon-γ (20 ng/ml). Inhibition of pre-adipocyte differentiation is evident from accumulation of lipid droplets during the course of the experiment.

In order to explore whether inflammatory mediators (produced in the vascular wall) modify directly the ability of PVAT's pre-adipocytes to differentiate, we then exposed human pre-adipocytes collected from PVAT to a combination of IL-6, TNF-α and IFNγ and induced their differentiation. We observed that these cytokines had a striking inhibitory effect on the ability of pre-adipocytes to differentiate to mature adipocytes as observed visually during the differentiation time-course (FIG. 19), and documented by the lower intracellular accumulation of lipid droplets (oil-red-O staining, FIGS. 16A-D) quantified using a photometric assay (FIG. 16E). The impact of these cytokines on the ability of pre-adipocytes to differentiate was then confirmed by quantifying the expression of PPARγ (FIG. 16G), CEBPA (FIG. 16H) and FABP4 (FIG. 16I)) during the differentiation time-course. The same cytokines also accelerated significantly the proliferation rate of the human pre-adipocytes, evaluated using the MTS assay (FIG. 16F). These findings support the notion that vessel-derived inflammatory cytokines may induce proliferation and inhibit the differentiation of human pre-adipocytes in the neighbouring perivascular adipose tissue, in a paracrine way. Therefore, if we develop non-invasive tools to monitor these phenotypic changes of PVAT driven by vascular inflammation, we may be able to identify inflammation in the coronary arteries non-invasively.

Evaluating Adipocyte Differentiation Status Using Computerized Tomography

Figure 17:
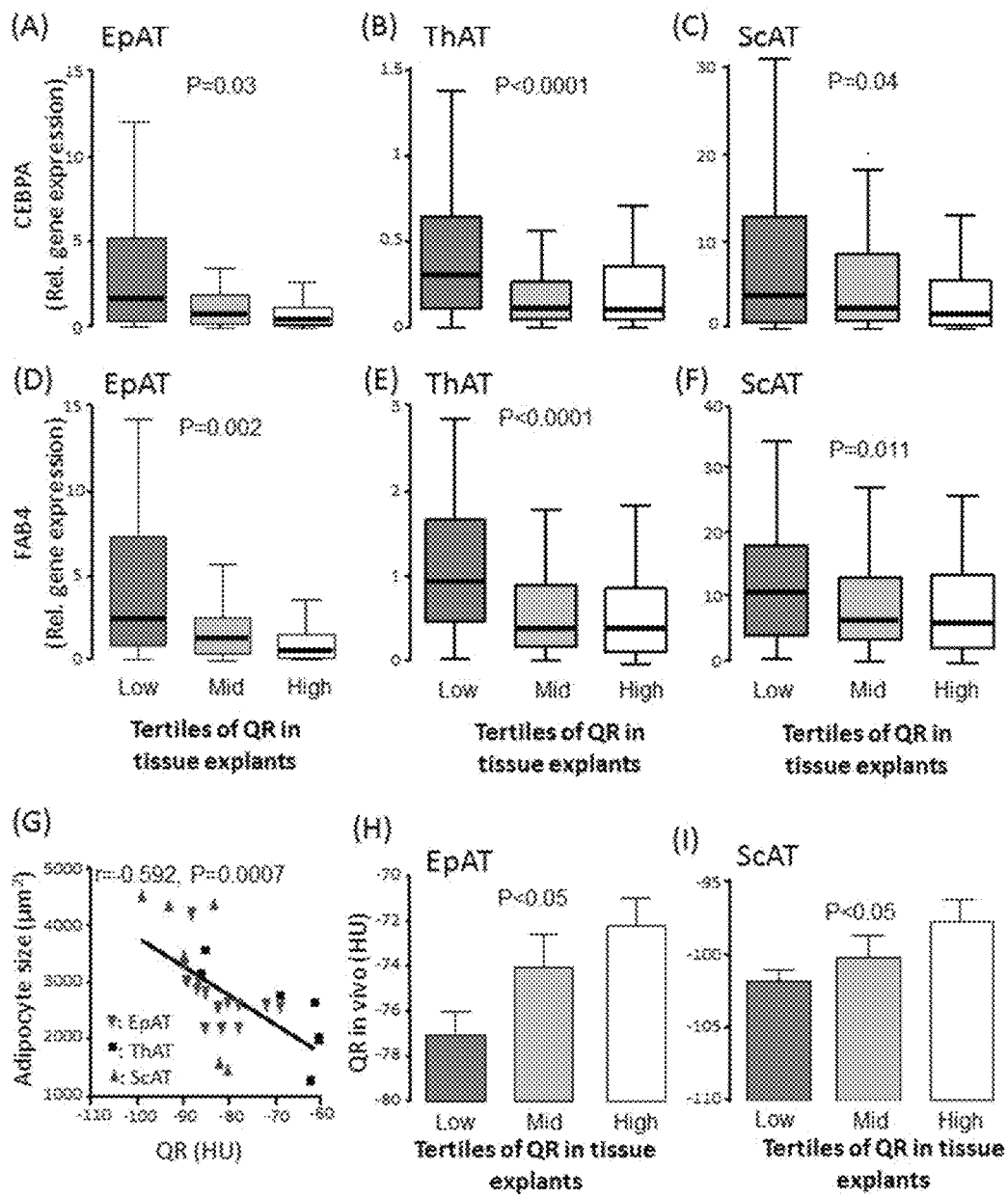
FIG. 17 shows gene expression analysis and average adipose tissue radiodensity (Quantified Radiodensity, QR) measurements in explants of epicardial (EpAT), thoracic (ThAT) and subcutaneous (ScAT) adipose tissue from 453 patients undergoing coronary-artery bypass grafting (Study Arm 1). Adipose tissue samples were scanned by computed tomography (CT) and QR for each sample was calculated as the average radiodensity of the fat (−190 to −30 Hounsfield Units). Each explant was divided into tertiles based on measured QR values. The range of QR in each tertile was: for EpAT (Low: −120 to −84.3 HU, Mid: −84.1 to −73.0 HU, High: −72.9 to −52.7 HU), for ThAT (Low: −125 to −77.7 HU, Mid: −77.6 to −68.7 HU, High: −68.6 to −49.8 HU) and for ScAT (Low: −128.0 to −84.4HU, Mid: −84.3 to −74.2 HU, High: −74.1 to −56.1 HU).

The balance between the lipid and aqueous phases of adipose tissue is reflected in adipocyte size (Di Girolamo M and Owens J L (1976). Water content of rat adipose tissue and isolated adipocytes in relation to cell size. *Am J Physiol* 231:1568-72). To explore whether the average CT radiodensity of adipose tissue (represented by the QR index described above) provides a marker of adipocytes differentiation status/size, we quantified QR in EpAT, ThAT and ScAT explants obtained from 453 patients undergoing cardiac surgery (study arm 1). There was a striking inverse association between QR and the degree of adipocyte differentiation as defined by the expression of CEBPA and FABP4 in the same samples (FIG. 17A-F). There was also a strong inverse association between the QR of adipose tissue explants and adipocyte size quantified by histology (FIG. 17G). Accordingly, we were reassured that QR may be used as a marker of the variation of adipocyte differentiation and size in different adipose tissue depots (i.e. the greater the adipocyte differentiation/size the more lipophilic the content of the tissue, therefore the more negative the QR). To address this hypothesis in vivo, we performed CT scans in a group of 105 patients from whom adipose tissue explants had been imaged ex vivo (from Study arm 1). We observed a strong correlation between the QR obtained in vivo and the respective QR measured in the explants of the same tissue from these patients (FIGS. 17H and I).

Figure 18:
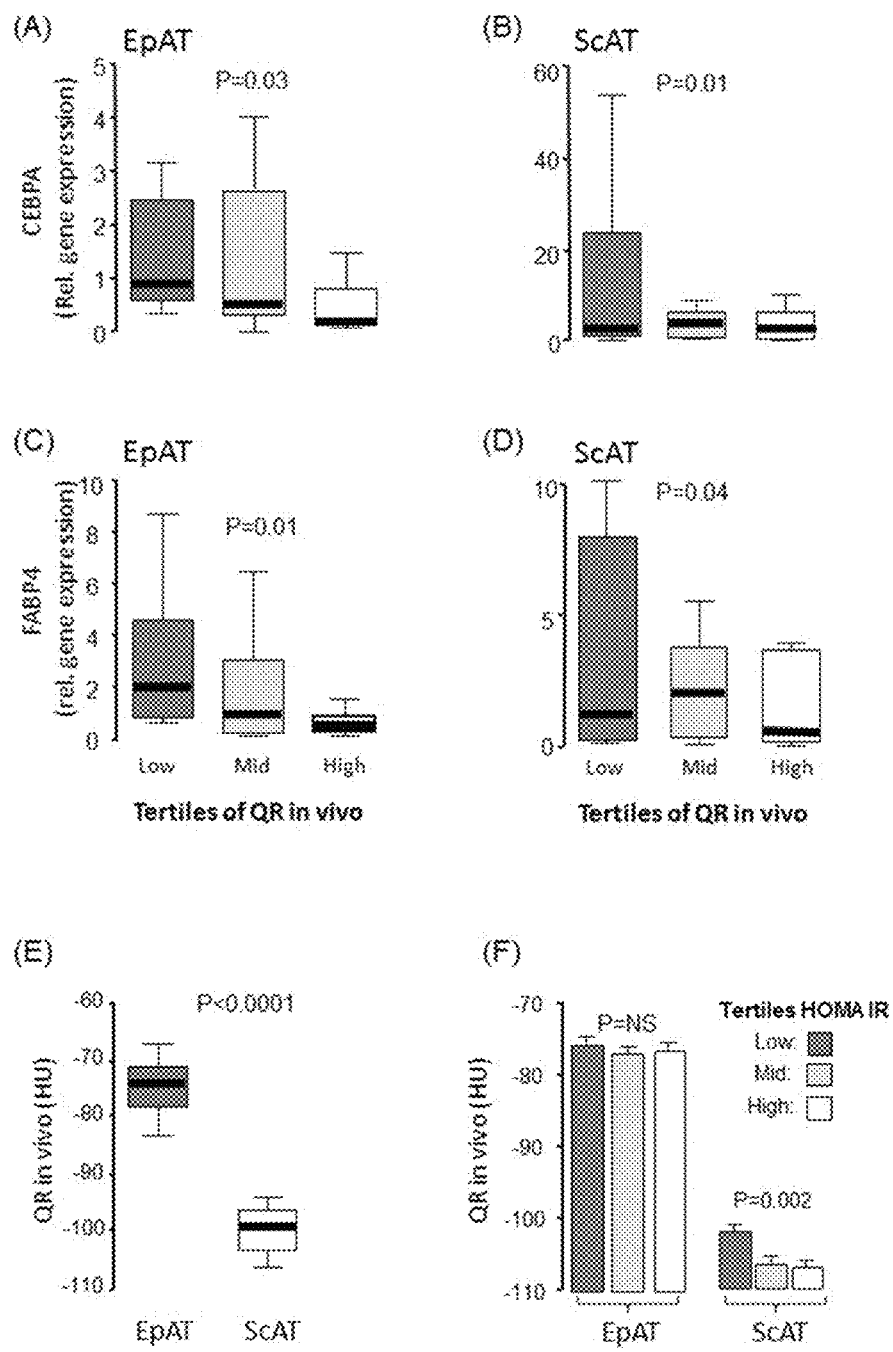
FIG. 18 shows gene expression analysis and average adipose tissue radiodensity (Quantified Radiodensity, QR) measurements in explants of epicardial (EpAT) and subcutaneous (ScAT) adipose tissue from 105 patients from Study Arm 1. Adipose tissue underwent computerised tomography angiography scanning (CT), while epicardial (EpAT) and subcutaneous (ScAT) adipose tissue samples were collected during surgery for gene expression studies to determine adipocyte differentiation status. In vivo QR was calculated for each adipose tissue depot as the average radiodensity of the fat (−190 to −30 Hounsfield Units). Each explant was divided into tertiles based on measured QR values. The range of QR in each tertile was: for EpAT (Low: −81.6 to −74.7 HU, Mid: −74.8 to −70.7 HU, High: −70.9 to −61.0 HU) and for ScAT (Low: −108 to −101 HU, Mid: −101 to −97 HU, High: −97 to −89 HU).

To further validate the ability of QR to estimate adipocyte differentiation status (hence adipocyte size) in vivo, we correlated the in vivo QR values for EpAT and ScAT from CT scans of 105 patients (as described above), with the expression of adipocyte differentiation markers. We observed that the in vivo QR was strongly related with the expression of both CEBPA (FIGS. 18A and B) and FABP4 (FIGS. 18C and D) in the respective adipose tissue depots from these patients. EpAT QR in vivo was significantly higher compared to ScAT QR in vivo (FIG. 18E), confirming that histologically demonstrated differences in adipose tissue depots differentiation status leads to respective differences in QR in vivo. Interestingly, HOMA-IR was positively associated with ScAT QR in vivo, but not with EpAT QR (FIG. 18F), suggesting that systemic metabolic status is linked to ScAT differentiation status/adipocyte size, whereas that of EpAT is highly regulated by local, rather than systemic stimuli.

Figure 15:
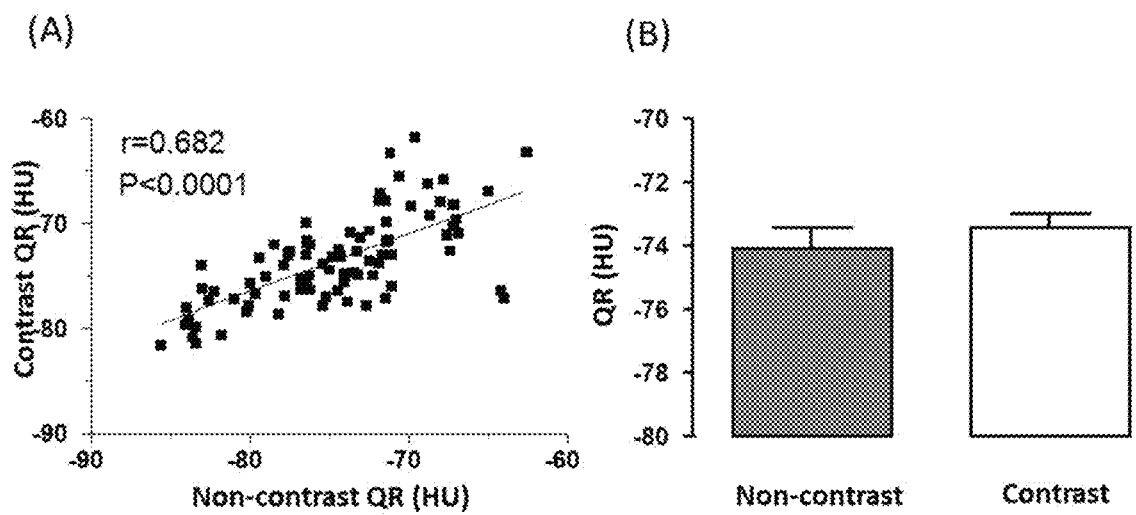
FIG. 15 shows association between average adipose tissue radiodensity (Quantified radiodensity, QR) in contrast and non-contrast computerised tomography (CT) images in epicardial adipose tissue (EpAT).

Technical Considerations:

Given that the CT scans are routinely performed using a contrast agent, we then explored the possible impact of the contrast agent on the obtained QR images in vivo, and document a strong linear relationship between the QR obtained from images with and without contrast agent administration (FIG. 15). Due to the high regional histological heterogeneity of ThAT, meaningful matching of in vivo CT images with the biological characteristics of the respective tissue biopsies was not possible. Therefore, QR as described so far provides a reliable marker of adipocyte differentiation status/size in vivo only in EpAT and ScAT.

Figure 20:
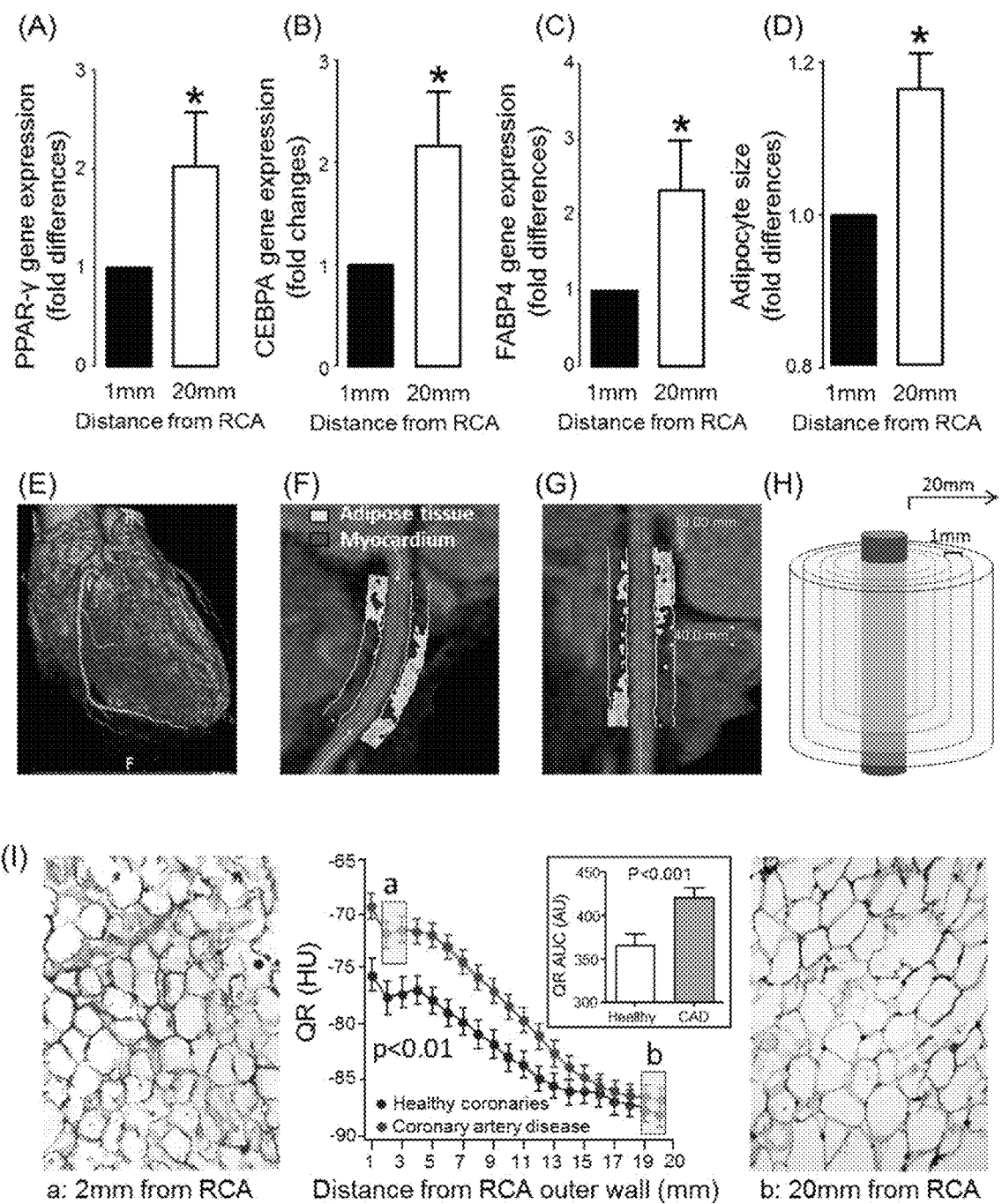
FIG. 20 shows analysis of peri-coronary adipose tissue samples in close proximity to the right coronary artery (RCA) and 2 cm away from it in 15 patients undergoing coronary artery bypass grafting (Study arm 2). Adipose tissue samples were used for gene expression studies to determine adipocyte differentiation status and for histology to determine adipocyte size.
Figure 22:
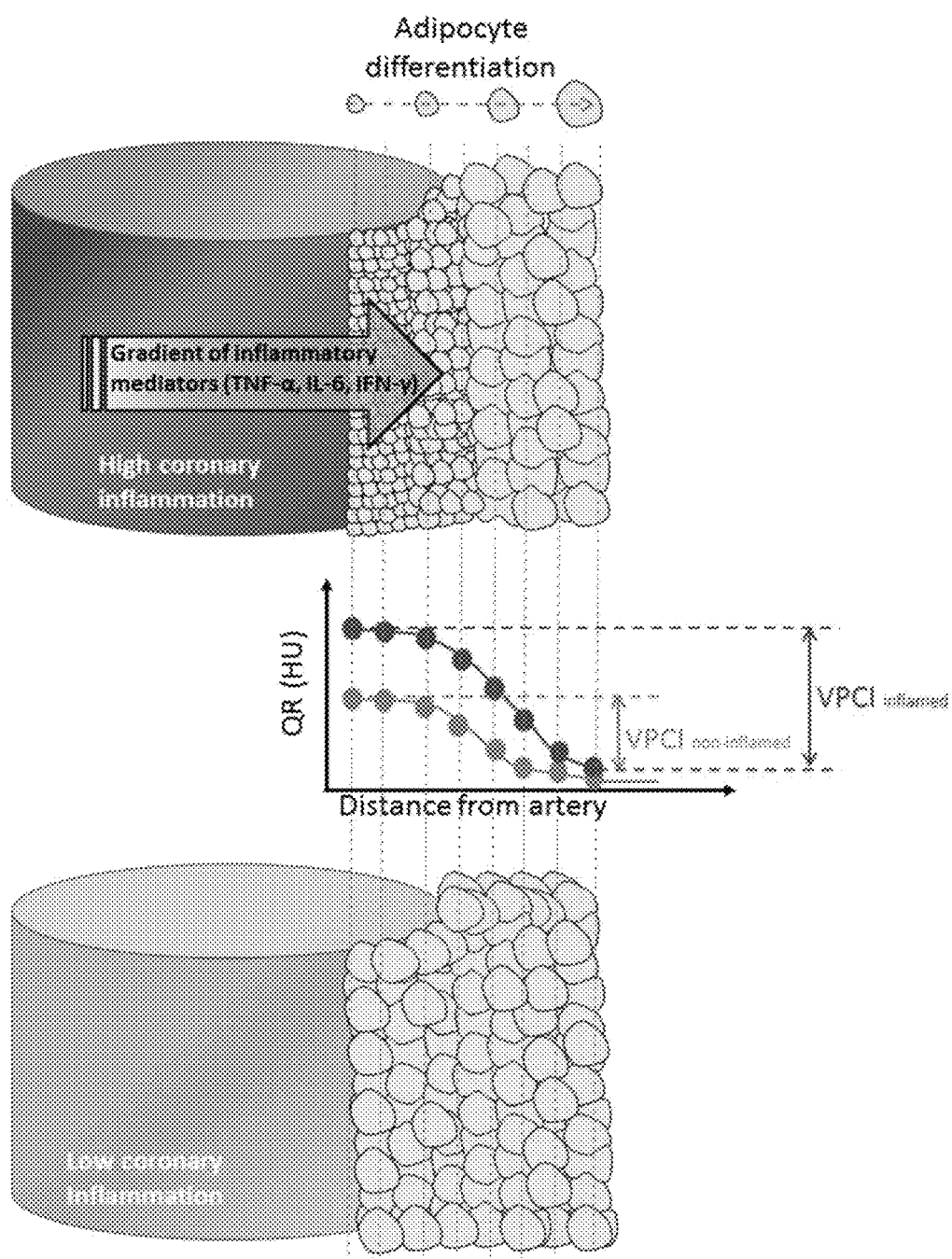
FIG. 22 shows that vascular inflammation results in higher expression and release of pro-inflammatory mediators from the arterial wall. Such pro-inflammatory stimuli act on the surrounding perivascular adipose tissue (PVAT) by triggering proliferation and inhibiting differentiation of preadipocytes to mature adipocytes, rendering the adipocytes closer to the inflamed vascular wall smaller in size and less differentiated compared to adipocytes that lie further away from the vessel. These biological effects of the "inflamed" vessels on their surrounding adipose tissue change PVAT hydrophilic/lipophilic content and can be detected by Computerized Tomography imaging as higher PVAT radiodensity (Quantified Radiodensity or $QR_{PVAT}$). The gradient of QR from PVAT to non-PVAT (20 mm away from the vessel wall) is described by the Volumetric Perivascular Characterization Index (VPCI), which is also different between inflamed and non-inflamed vessels.

Visualising the Changes of Adipocyte Size/Differentiation Status in Peri-Coronary Adipose Tissue In Vivo To investigate the relationship between QR and adipocyte size/differentiation status around the human coronary arteries, we compared adipose tissue from immediately adjacent to the right coronary artery (RCA) with adipose 2 cm away from the RCA, not in proximity with any visible epicardial coronary branch, from patients undergoing CABG in study arm 2. We first observed that the expression of PPAR-y, CEBPA and FABP4 was significantly downregulated closer to the RCA (FIG. 20A-C). Similarly, adipocyte size was significantly smaller in proximity to the right coronary artery compared to the adipocyte size 2 cm away from the vascular wall (FIG. 20D). These observations confirmed our findings from the ex vivo and in vitro experiments, showing that inflammatory signals from the diseased human coronary artery prevent the differentiation of pre-adipocytes in PVAT adjacent to it, creating a gradient of this effect in the adipose tissue surrounding the coronary arterial tree See FIG. 22). To examine whether we could track these morphological changes of PVAT in response to coronary inflammation by non-invasive CT imaging, we used our newly developed imaging analysis tools, to analyse the CT angiographic images of a further clinical cohort of 273 subjects in study arm 3 (156 with and 117 without significant coronary atherosclerosis, study arm 3). We quantified QR around the proximal segment of the right coronary, in 3D cylindrical layers of 1 mm thickness, from immediately adjacent to the vascular wall, moving to 20 mm away from the vascular wall (FIG. 20E-H). We observed a progressive decrease of QR to more negative values as moving from close to the vessel to adipose tissue away from it (FIG. 20I), confirming that QR tracks accurately the changes in adipocyte size and differentiation status. Importantly, the relationships between QR and distance from the vascular wall were significantly different in patients with coronary atherosclerosis compared to healthy individuals, showing lower QR values close to the vascular wall of healthy individuals compatible with larger, more differentiated adipocytes (FIG. 20A-I). This suggests that the observed changes of QR could actually characterise the degree of vascular inflammation inside the human coronaries, detectable using a novel, non-invasive approach in vivo.

Figure 21:
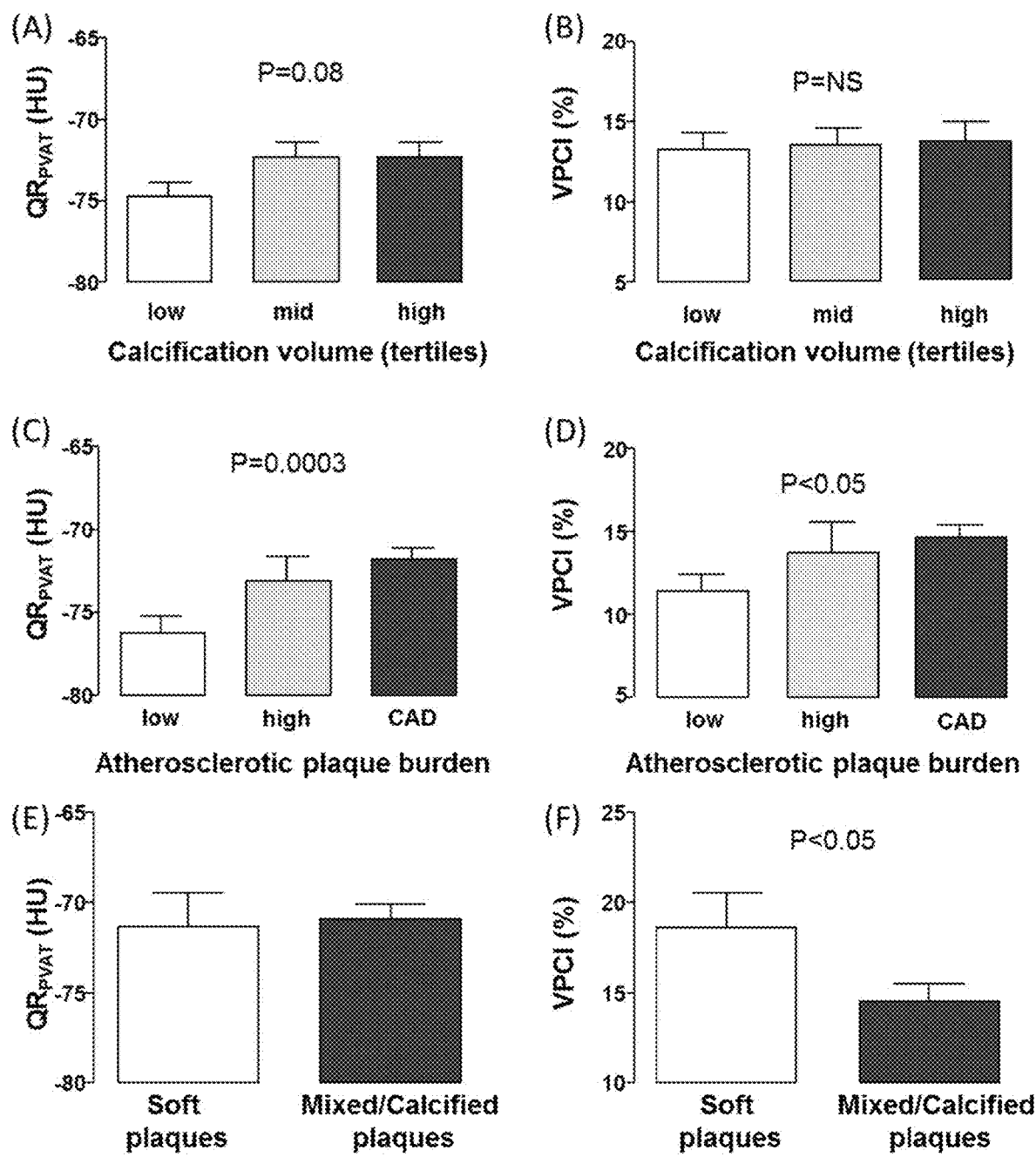
FIG. 21 shows analysis of PVAT average radiodensity (quantified radiodensity of PVAT-$QR_{PVAT}$) and VPCI % values [from patients in study arm 3. Total and right coronary artery (RCA) calcium score were calculated from CT angiography, and a 40 mm segment of the proximal RCA (10 mm after its ostial origin) was tracked for further analysis of the surrounding perivascular adipose tissue (PVAT) and the underlying vascular segment. $QR_{PVAT}$ was calculated as the average adipose tissue radiodensity (−190 to −30HU, lying in a radial distance from the outer vascular wall equal to average vessel diameter) and corresponding VPCI % values were calculated as the percent difference between each individual $QRP_{VAT}$ value and the QR of epicardial adipose tissue 2 cm away from the RCA.

Validating QR and VPCI Against Established Imaging Biomarkers with Clinical Predictive Value To validate QR against established imaging biomarkers with known clinical predictive value, we quantified CCS (in the RCA and globally in the entire coronary tree) and Fibrous plaque index in the RCA, in the 273 individuals in study arm 3. There was a significant correlation between QR and calcium score (FIGS. 21A and B), but the ability of QR to discriminate subjects with non-detectable from those with detectable but low calcium was rather limited. VPCI (the gradient of QR from PVAT to non-PVAT) was superior as a biomarker in identifying subjects with intermediate coronary calcium score (either total (FIG. 21C) or specifically in the RCA (FIG. 21D)). Importantly, both QR and VPCI were strongly related with fibrous plaque index of the underlying RCA (FIGS. 21E and F).

The invention claimed is:

1. A method for detecting inflammation of a blood vessel by volumetric characterisation of perivascular adipose tissue surrounding the blood vessel from a length of computed tomography (CT) scanned blood vessel in a patient; the method comprising:

gathering data from a computed tomography scan of the perivascular adipose tissue surrounding the scanned blood vessel along the length of the scanned blood vessel;

volumetrically characterizing with a processor only the perivascular adipose tissue using the data gathered by the computed tomography scan, wherein the characterized perivascular adipose tissue consists of one or more concentric layers of adipose tissue surrounding the length of the scanned blood vessel;

quantifying radiodensity values as attenuation in each of the one or more concentric layers of perivascular adipose tissue surrounding the length of the scanned blood vessel;

determining whether one or more of the quantified radiodensity values are above or below a baseline radiodensity value; and administering a therapy to the patient to treat or prevent vascular disease based on whether the quantified radiodensity values of the characterized perivascular tissue are above or below the baseline radiodensity value.

2. The method according to claim 1, wherein the quantified radiodensity is quantified for water in the each of one or more concentric layers of perivascular adipose tissue.

3. The method according to claim 1, wherein the quantified radiodensity is an average radiodensity.

4. The method according to claim 3, wherein the data is gathered from the computed tomography scan along a 4 cm length, starting 1 cm distally to the origin of the right coronary artery.

5. The method according to claim 1, wherein the data is gathered from the computed tomography scan along a length of the right coronary artery, left anterior descending artery, left circumflex artery, aorta, carotid arteries or femoral arteries.

6. The method according to claim 1, wherein the data is gathered from the computed tomography scan along a length of the aorta.

7. The method according to claim 1, wherein the each of one or more concentric layers of perivascular adipose tissue are 1 mm thick.

8. The method according to claim 1, wherein the each of one or more concentric layers of perivascular adipose tissue extend to an end distance from the outer wall of the blood vessel, the end distance being the point where radiodensity of adipose tissue reaches a minimum value within a scanned anatomical area in a healthy vessel or drops by >10% vs the baseline radiodensity value, in a vessel of the same type free of disease.

9. The method according to claim 8, wherein the each of one or more concentric layers of perivascular adipose tissue extend to an end distance of 10 mm from the outer wall of the blood vessel.

10. The method according to claim 8, wherein the each of one or more concentric layers of perivascular adipose tissue extend to an end distance of 20 mm from the outer wall of the blood vessel.

11. The method according to claim 1, wherein the baseline radiodensity value is average radiodensity quantified in a layer of perivascular adipose tissue lying within the first 1 mm-thick concentric layer surrounding the outer vessel wall.

12. The method according to claim 11, wherein the baseline radiodensity is radiodensity quantified for adipose tissue in a layer of perivascular adipose tissue lying proximal to the outer wall of the blood vessel; and wherein the adipose tissue in the layer lying proximal corresponds to voxels having an attenuation of −190 to −30 Hounsfield Units (HU).

13. The method according to claim 11, wherein the baseline radiodensity is radiodensity quantified for water in a layer of perivascular adipose tissue lying proximal to the outer wall of the blood vessel; and wherein the water corresponds to voxels having an attenuation of −15 to +15 Hounsfield Units (HU).

14. The method according to claim 1, further comprising:
determining a plot of a fold change in the quantified radiodensity relative to baseline radiodensity in the each of one or more concentric layers of perivascular adipose tissue with respect to distance from the outer wall of the blood vessel up to an end distance;
determining an area of a region bound by the plot of fold change in the quantified radiodensity and a plot of baseline radiodensity with respect to the distance from the outer wall of the blood vessel up to the end distance; and
dividing said area by the quantified radiodensity measured at the distance from the outer wall of the blood vessel, wherein the distance is less than the radius of the vessel or is a distance from the outer surface of the vessel above which the quantified radiodensity of adipose tissue drops by more than 5% compared to baseline radiodensity of adipose tissue in a vessel of the same type free of disease.

15. The method according to claim 14, wherein the quantified radiodensity is quantified radiodensity of adipose tissue in the each of one or more concentric layers of perivascular adipose tissue.

16. The method according to claim 14, wherein the quantified radiodensity is quantified radiodensity of water in the each of one or more concentric layers of perivascular adipose tissue.

17. The method according to claim 14, wherein the quantified radiodensity is an average radiodensity.

18. The method according to claim 14, wherein the end distance is the point where radiodensity of adipose tissue reaches a minimum value within a scanned anatomical area in a healthy vessel or drops by >10% below the baseline radiodensity value, in a vessel of the same type free of disease.

19. The method according to claim 18, wherein the end distance is 10 mm.

20. The method according to claim 18, wherein the end distance is 20 mm.

21. The method according to claim 1, further comprising:
subtracting quantified radiodensity in a layer of non-perivascular adipose tissue from the quantified radiodensity in a layer of perivascular adipose tissue located at a distance equal to the radius of the vessel around the outer wall of the blood vessel.

22. The method according to claim 21, wherein the quantified radiodensity in a layer of perivascular adipose tissue is quantified radiodensity of adipose tissue in the layer of perivascular adipose tissue located at the distance equal to the radius.

23. The method according to claim 21, wherein the quantified radiodensity in a layer of non-perivascular tissue is quantified radiodensity of adipose tissue in the layer of non-perivascular tissue located at the distance equal to the radius.

24. The method according to claim 21, wherein the quantified radiodensity in a layer of perivascular adipose tissue is quantified radiodensity of water in the layer of perivascular adipose tissue.

25. The method according to claim 21, wherein the quantified radiodensity in a layer of non-perivascular tissue is quantified radiodensity of water in the layer of non-perivascular tissue.

26. The method according to claim 21, wherein the quantified radiodensity in a layer of perivascular adipose tissue is an average radiodensity.

27. The method according to claim 21, wherein the quantified radiodensity in a layer of non-perivascular adipose tissue is an average radiodensity.

28. The method according to claim 21, wherein the quantified radiodensity in a layer of non-perivascular tissue is radiodensity measured in a layer of non-perivascular tissue located at a distance greater than an average radius of the vessel around the outer wall of the blood vessel.

29. The method according to claim 21, wherein the quantified radiodensity in a layer of non-perivascular tissue is radiodensity measured in a layer of non-perivascular tissue located at a distance equal to three times an average radius of the vessel around the outer wall of the blood vessel.

30. The method according to claim 21, further comprising assigning a determined value of a difference between the quantified radiodensity in a layer of perivascular adipose tissue and the quantified radiodensity in a layer of non-perivascular tissue to a scale having a lower threshold and a higher threshold.

31. The method according to claim 30, wherein the lower threshold is a value between the lowest and mid tertile.

32. The method according to claim 31, wherein the lower threshold is 2.

33. The method according to claim 30, wherein the upper threshold is a value between the mid and highest tertile.

34. The method according to claim 33, wherein the upper threshold is 8.

35. The method according to claim 1, wherein the step of gathering data from the computed tomography scan along the length of the scanned blood vessel comprises gathering images from the computed tomography scan.

36. The method according to claim 1, further comprising determining whether the scanned blood vessel is an inflamed blood vessel and has released mediators exerting a paracrine effect on the perivascular adipose tissue surrounding the inflamed scanned blood vessel.

37. A method for detecting inflammation of a blood vessel by volumetric characterization of perivascular adipose tissue surrounding the blood vessel to guide treatment for prevention or management of vascular tissue; the method comprising:
conducting a computed tomography scan of the perivascular adipose tissue surrounding a wall of the blood vessel of a length of blood vessel in a patient;
gathering data from the computed tomography scan along and surrounding the length of the scanned blood vessel;
volumetrically characterizing with a processor only the perivascular adipose tissue using the data gathered by the computed tomography scan, wherein the characterized perivascular adipose tissue consists of one or more concentric layers of adipose tissue surrounding the length of the scanned blood vessel;
quantifying radiodensity values comprising attenuation in each of the one or more concentric layers of perivascular adipose tissue surrounding the length of the scanned blood vessel;

determining whether one or more of the quantified radiodensity values are above or below a baseline radiodensity value; and administering a therapy to the patient to treat or prevent vascular disease based on whether the quantified radiodensity values of the characterized perivascular tissue are above or below the baseline radiodensity value.

38. The method according to claim 37, further comprising determining whether the scanned blood vessel is an inflamed blood vessel and has released mediators exerting a paracrine effect on the perivascular adipose tissue surrounding the inflamed scanned blood vessel.

\* \* \* \* \*